(12) United States Patent
Son et al.

(10) Patent No.: US 12,409,364 B2
(45) Date of Patent: Sep. 9, 2025

(54) ELECTRONIC DEVICE FOR PROVIDING EXERCISE CONTENT BASED ON RECOGNITION SPACE AND OPERATING METHOD THEREOF

(71) Applicant: SAMSUNG ELECTRONICS CO., LTD., Suwon-si (KR)

(72) Inventors: Taehwan Son, Suwon-si (KR); Jeongmin Park, Suwon-si (KR); Daesung Cho, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 364 days.

(21) Appl. No.: 18/121,656

(22) Filed: Mar. 15, 2023

(65) Prior Publication Data

US 2023/0249033 A1 Aug. 10, 2023

Related U.S. Application Data

(63) Continuation of application No. PCT/KR2022/018774, filed on Nov. 24, 2022.

(30) Foreign Application Priority Data

Feb. 8, 2022 (KR) .................. 10-2022-0016364
Mar. 30, 2022 (KR) .................. 10-2022-0039654

(51) Int. Cl.
*A63B 24/00* (2006.01)
*A63B 71/06* (2006.01)
(Continued)

(52) U.S. Cl.
CPC ...... *A63B 24/0075* (2013.01); *A63B 24/0062* (2013.01); *A63B 71/0622* (2013.01);
(Continued)

(58) Field of Classification Search
CPC ............ A63B 24/0075; A63B 24/0062; A63B 71/0622; A63B 2220/836; A63B 2225/54;
(Continued)

(56) References Cited

U.S. PATENT DOCUMENTS 7,217,224 B2 * 5/2007 Thomas .................. H04L 67/12
482/8
8,419,545 B2 4/2013 Yen et al.
(Continued)

FOREIGN PATENT DOCUMENTS

JP 4907483 3/2012
JP 5138833 2/2013
(Continued)

OTHER PUBLICATIONS

International Search Report for PCT/KR2022/018774, mailed Mar. 7, 2023, 3 pages.

*Primary Examiner* — Garrett K Atkinson
(74) *Attorney, Agent, or Firm* — Nixon & Vanderhye, P.C.

(57) ABSTRACT

An example electronic device may include a plurality of antennas for wireless communication, a processor configured to scan to identify whether there is at least one portable device using the plurality of antennas, define a three-dimensional recognition space based on a first signal for space setting transmitted from a portable device identified by the scan, calculate a position of the identified portable device in the recognition space based on a second signal transmitted from the identified portable device, and generate exercise content based on the position of the identified portable device, and a display module, including a display, configured to display the exercise content.

20 Claims, 17 Drawing Sheets

(51) Int. Cl.
  *G01S 5/06* (2006.01)
  *G06F 3/01* (2006.01)

(52) U.S. Cl.
  CPC ............... *G01S 5/06* (2013.01); *G06F 3/011* (2013.01); *A63B 2220/836* (2013.01); *A63B 2225/54* (2013.01)

(58) Field of Classification Search
  CPC ....... A63B 71/06; G01S 5/06; G01S 2205/01; G01S 2205/08; G01S 5/0284; G01S 5/14; G06F 3/011; G06F 3/01; G06Q 50/10; A61B 5/11; A61B 5/681; H04W 4/02; G09B 19/0038
  See application file for complete search history.

(56) References Cited

U.S. PATENT DOCUMENTS

| | | | | |
|---|---|---|---|---|
| 9,108,098 | B2* | 8/2015 | Galasso | G06Q 30/0255 |
| 9,288,368 | B2* | 3/2016 | O'Sullivan | H04N 5/04 |
| 10,024,948 | B2 | 7/2018 | Ganick et al. | |
| 11,998,316 | B2* | 6/2024 | Park | A61B 5/743 |
| 12,002,179 | B2* | 6/2024 | Palacios | A63B 24/0006 |
| 2004/0102931 | A1* | 5/2004 | Ellis | A61B 5/0833 |
| | | | | 702/188 |
| 2005/0239601 | A1* | 10/2005 | Thomas | A63B 24/00 |
| | | | | 482/8 |
| 2007/0061076 | A1* | 3/2007 | Shulman | G06T 7/97 |
| | | | | 701/500 |
| 2009/0011907 | A1* | 1/2009 | Radow | B62M 3/00 |
| | | | | 482/57 |
| 2009/0098524 | A1* | 4/2009 | Walton | G09B 5/14 |
| | | | | 434/350 |
| 2009/0221374 | A1 | 9/2009 | Yen et al. | |
| 2010/0269143 | A1* | 10/2010 | Rabowsky | H04B 7/18591 |
| | | | | 725/63 |
| 2014/0049636 | A1* | 2/2014 | O'Donnell | G08B 13/19641 |
| | | | | 348/143 |
| 2014/0228982 | A1* | 8/2014 | Bharwani | E02F 9/261 |
| | | | | 700/56 |
| 2015/0098021 | A1* | 4/2015 | O'Sullivan | H04N 21/4223 |
| | | | | 348/516 |
| 2016/0119590 | A1 | 4/2016 | Ganick et al. | |
| 2016/0271796 | A1* | 9/2016 | Babu | B25J 9/1664 |
| 2017/0034430 | A1* | 2/2017 | Fu | H04N 23/70 |
| 2018/0255233 | A1* | 9/2018 | Shibata | H04N 23/695 |
| 2022/0347548 | A1* | 11/2022 | Watterson | A63B 22/0235 |

FOREIGN PATENT DOCUMENTS

| | | |
|---|---|---|
| KR | 10-2015-0001433 | 1/2015 |
| KR | 10-2016-0079664 | 7/2016 |
| KR | 10-2017-0040039 | 4/2017 |
| KR | 10-2018-0043866 | 5/2018 |
| KR | 10-2019-0135870 | 12/2019 |
| WO | 2010/143359 | 12/2010 |
| WO | 2020/214758 | 10/2020 |

* cited by examiner

ELECTRONIC DEVICE FOR PROVIDING EXERCISE CONTENT BASED ON RECOGNITION SPACE AND OPERATING METHOD THEREOF

CROSS-REFERENCE TO RELATED APPLICATIONS

This application is a continuation application of International Application No. PCT/KR2022/018774 designating the United States, filed on Nov. 24, 2022, in the Korean Intellectual Property Receiving Office and claiming priority to Korean Patent Application No. 10-2022-0016364, filed on Feb. 8, 2022, and Korean Patent Application No. 10-2022-0039654, filed on Mar. 30, 2022, in the Korean Intellectual Property Office, the disclosures of which are incorporated by reference herein in their entireties.

BACKGROUND

1. Field

Various embodiments of the following disclosure relate to an electronic device for providing exercise content based on a recognition space and an operating method thereof.

2. Description of Related Art

Portable devices include not only devices carried by a user, for example, smartphones or laptops, but also electronic devices attached to a body of a user for use. A portable device may take the form of, for example, glasses, a watch, or a head-mounted display (HMD), and may be connected to a smartphone or may independently perform various functions. A user may more conveniently perform, through a portable device, various tasks, for example, checking a simple text message or e-mail, health care and fitness management (such as checking a heart rate during exercise and calculating an exercise goal), and scheduling.

SUMMARY

Embodiments of the disclosure provide an electronic device that may set a three-dimensional recognition space based on a signal transmitted from a portable device.

Embodiments of the disclosure provide an electronic device that may calculate a relative position including a distance and an angle between the electronic device and a portable device in a recognition space using a difference in times at which a plurality of antennas receive a signal transmitted from the portable device.

Embodiments of the disclosure provide an electronic device that may generate exercise content including a character corresponding to a user wearing a portable device based on a relative position with the portable device in a recognition space.

Embodiments of the disclosure provide an electronic device that may adjust characters, exercise information, and the sizes of the characters displayed on a screen by reflecting movements of users.

The goals to be achieved are not limited to those described above and may be expanded in various manners within the scope of the disclosure without departing from the spirit and field of the disclosure.

According to an embodiment, an electronic device includes a plurality of antennas for wireless communication, a processor configured to scan to identify whether there is at least one portable device using the plurality of antennas, define a three-dimensional recognition space based on a first signal for space setting transmitted from a portable device identified by the scan, calculate a position of the identified portable device in the recognition space based on a second signal transmitted from the identified portable device, and generate exercise content based on the position of the identified portable device, and a display module configured to display the exercise content.

According to an embodiment, an operating method of an electronic device may include scanning to identify whether there is at least one portable device using a plurality of antennas for wireless communication, defining a three-dimensional recognition space based on a first signal for space setting transmitted from the identified portable device, calculating a position of the identified portable device in the recognition space based on a second signal transmitted from the identified portable device, generating exercise content based on the position of the identified portable device, and displaying the exercise content.

According to embodiments, an electronic device may provide exercise content including a character reflecting a physical action of a user wearing a portable device based on a relative position with the portable device.

According to embodiments, an electronic device may allow control of exercise content through intuitive motions and also display exercise content based on a relative position between users during a group exercise that the multiple users participate in, thereby increasing the immersion of the users performing an exercise.

According to embodiments, an electronic device may adjust characters, exercise information, and sizes of the characters displayed on a screen by reflecting movements of users, thereby allowing the users to three-dimensionally experience the movements in a recognition space.

According to embodiments, an electronic device may set a virtual recognition space, thereby freely setting the activity radius of users without the constraints of space due to the camera angle. In addition, various effects directly or indirectly ascertained through the present disclosure may be provided.

BRIEF DESCRIPTION OF THE DRAWINGS

The above and other aspects, features, and advantages of certain embodiments of the present disclosure will be more apparent from the following detailed description, taken in conjunction with the accompanying drawings, in which.

DETAILED DESCRIPTION

Figure 1:
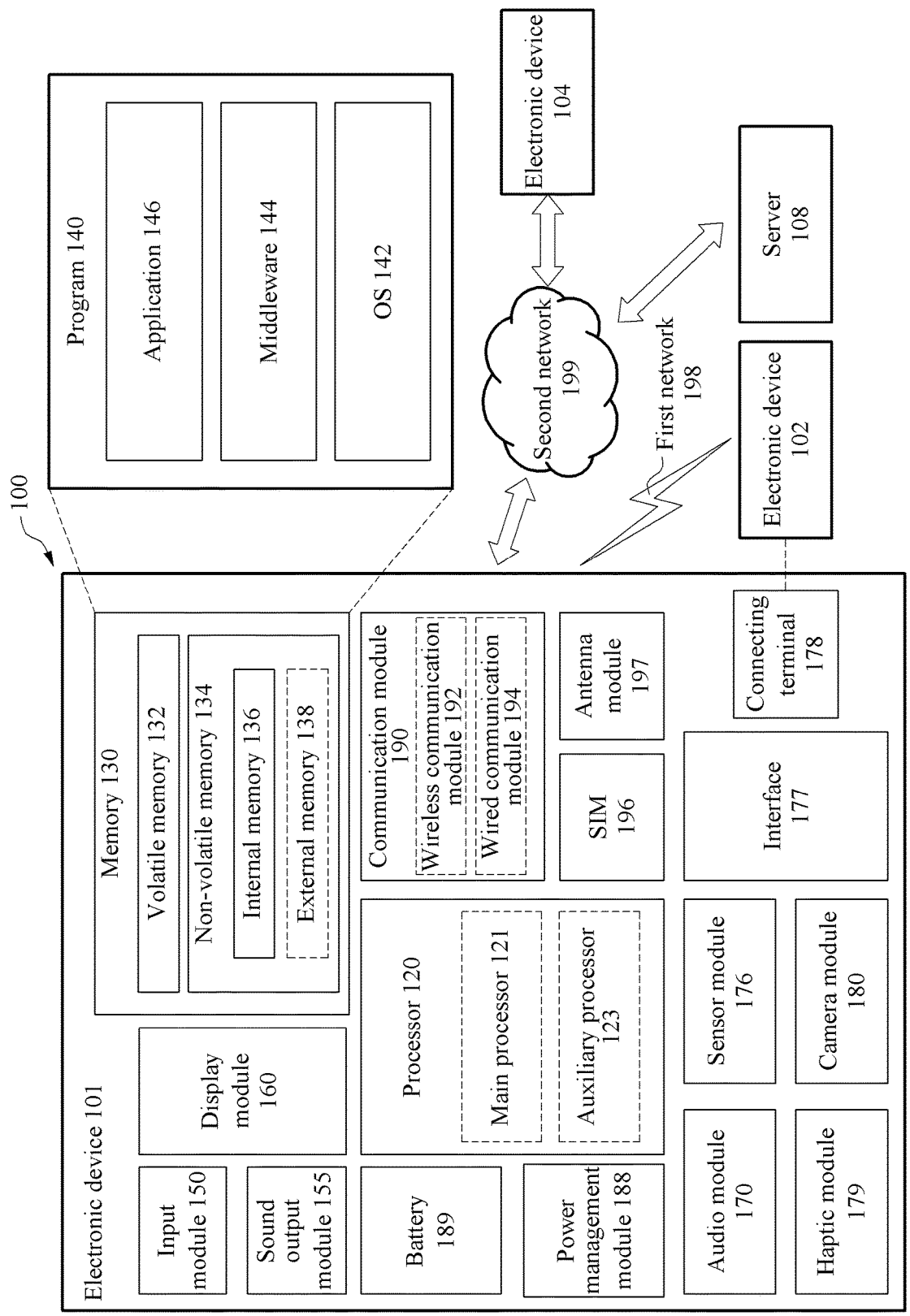
FIG. 1 is a block diagram illustrating an electronic device in a network environment according to one embodiment.

Hereinafter, various embodiments of the disclosure will be described in detail with reference to the accompanying drawings. When describing example embodiments with reference to the accompanying drawings, like reference numerals refer to like components and a description related thereto will not be repeated. However, this is not intended to limit the techniques disclosed herein to specific embodiments, and it should be understood that various modifications, equivalents, and/or alternatives of the embodiments of the disclosure are included. In connection with the description of the drawings, like reference numerals may be used for like components.

FIG. 1 is a block diagram illustrating an electronic device 101 in a network environment 100 according to one embodiment. Referring to FIG. 1, the electronic device 101 in the network environment 100 may communicate with an electronic device 102 via a first network 198 (e.g., a short-range wireless communication network), or communicate with at least one of an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, a memory 130, an input module 150, a sound output module 155, a display module 160, an audio module 170, and a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be integrated as a single component (e.g., the display module 160).

The processor 120 may execute, for example, software (e.g., a program 140) to control at least one other component (e.g., a hardware or software component) of the electronic device 101 connected to the processor 120, and may perform various data processing or computation. According to an embodiment, as at least a part of data processing or computation, the processor 120 may store a command or data received from another component (e.g., the sensor module 176 or the communication module 190) in a volatile memory 132, process the command or the data stored in the volatile memory 132, and store resulting data in a non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with the main processor 121. For example, when the electronic device 101 includes the main processor 121 and the auxiliary processor 123, the auxiliary processor 123 may be adapted to consume less power than the main processor 121 or to be specific to a specified function. The auxiliary processor 123 may be implemented separately from the main processor 121 or as a portion of the main processor 121.

The auxiliary processor 123 may control at least some of functions or states related to at least one (e.g., the display module 160, the sensor module 176, or the communication module 190) of the components of the electronic device 101, instead of the main processor 121 while the main processor 121 is in an inactive (e.g., sleep) state or along with the main processor 121 while the main processor 121 is an active state (e.g., executing an application). According to an embodiment, the auxiliary processor 123 (e.g., an ISP or a CP) may be implemented as a portion of another component (e.g., the camera module 180 or the communication module 190) that is functionally related to the auxiliary processor 123. According to an embodiment, the auxiliary processor 123 (e.g., an NPU) may include a hardware structure specified for artificial intelligence model processing. An artificial intelligence model may be generated by machine learning. Such learning may be performed by, for example, the electronic device 101 in which an artificial intelligence model is executed, or performed via a separate server (e.g., the server 108). Learning algorithms may include, but are not limited to, for example, supervised learning, unsupervised learning, semi-supervised learning, or reinforcement learning. The artificial intelligence model may include a plurality of artificial neural network layers. An artificial neural network may include, for example, a deep neural network (DNN), a convolutional neural network (CNN), a recurrent neural network (RNN), a restricted Boltzmann machine (RBM), a deep belief network (DBN), and a bidirectional recurrent deep neural network (BRDNN), a deep Q-network, or a combination of two or more thereof, but is not limited thereto. The artificial intelligence model may additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored as software in the memory 130, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output a sound signal to the outside of the electronic device 101. The sound output module 155 may include, for example, a speaker or a receiver. The speaker may be used for general purposes, such as playing multimedia or playing record. The receiver may be used to receive an incoming call. According to an embodiment, the receiver may be implemented separately from the speaker or as a part of the speaker.

The display module 160 may visually provide information to the outside (e.g., a user) of the electronic device 101. The display module 160 may include, for example, a control circuit for controlling a display, a hologram device, or a projector and control circuitry to control a corresponding one of the display, the hologram device, and the projector. According to an embodiment, the display module 160 may include a touch sensor adapted to detect a touch, or a pressure sensor adapted to measure the intensity of force incurred by the touch.

The audio module 170 may convert a sound into an electrical signal or vice versa. According to an embodiment, the audio module 170 may obtain the sound via the input module 150 or output the sound via the sound output module 155 or an external electronic device (e.g., the electronic device 102 such as a speaker or a headphone) directly or wirelessly connected to the electronic device 101.

The sensor module 176 may detect an operational state (e.g., power or temperature) of the electronic device 101 or an environmental state (e.g., a state of a user) external to the electronic device 101, and generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high-definition multimedia interface (HDMI), a universal serial bus (USB) interface, a secure digital (SD) card interface, or an audio interface.

The connecting terminal 178 may include a connector via which the electronic device 101 may be physically connected to an external electronic device (e.g., the electronic device 102). According to an embodiment, the connecting terminal 178 may include, for example, an HDMI connector, a USB connector, an SD card connector, or an audio connector (e.g., a headphone connector).

The haptic module 179 may convert an electrical signal into a mechanical stimulus (e.g., a vibration or a movement) or an electrical stimulus which may be recognized by a user via his or her tactile sensation or kinesthetic sensation. According to an embodiment, the haptic module 179 may include, for example, a motor, a piezoelectric element, or an electric stimulator.

The camera module 180 may capture a still image and moving images. According to an embodiment, the camera module 180 may include one or more lenses, image sensors, image signal processors, or flashes.

The power management module 188 may manage power supplied to the electronic device 101. According to an embodiment, the power management module 188 may be implemented as, for example, at least a part of a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently of the processor 120 (e.g., an AP) and that support a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module, or a power line communication (PLC) module). A corresponding one of these communication modules may communicate with the external electronic device 104 via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., a LAN or a wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the SIM 196.

The wireless communication module 192 may support a 5G network after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., a mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), an array antenna, analog beam-forming, or a large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element including a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in a communication network, such as the first network 198 or the second network 199, may be selected by, for example, the communication module 190 from the plurality of antennas. The signal or the power may be transmitted or received between the communication module 190 and the external electronic device via the at least one selected antenna. According to an embodiment, another component (e.g., a radio frequency integrated circuit (RFIC)) other than the radiating element may be additionally formed as a part of the antenna module 197.

According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the external electronic devices 102 and 104 may be a device of the same type as or a different type from the electronic device 101. According to an embodiment, all or some of operations to be executed by the electronic device 101 may be executed at one or more of the external electronic devices 102 and 104, and the server 108. For example, if the electronic device 101 needs to perform a function or a service automatically, or in response to a request from a user or another device, the electronic device 101, instead of, or in addition to, executing the function or the service, may request one or more external electronic devices to perform at least part of the function or the service. The one or more external electronic devices receiving the request may perform the at least portion of the function or the service requested, or an additional function or an additional service related to the request, and may transfer an outcome of the performing to the electronic device 101. The electronic device 101 may provide the outcome, with or without further processing of the outcome, as at least portion of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In an embodiment, the external electronic device 104 may include an Internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2A:
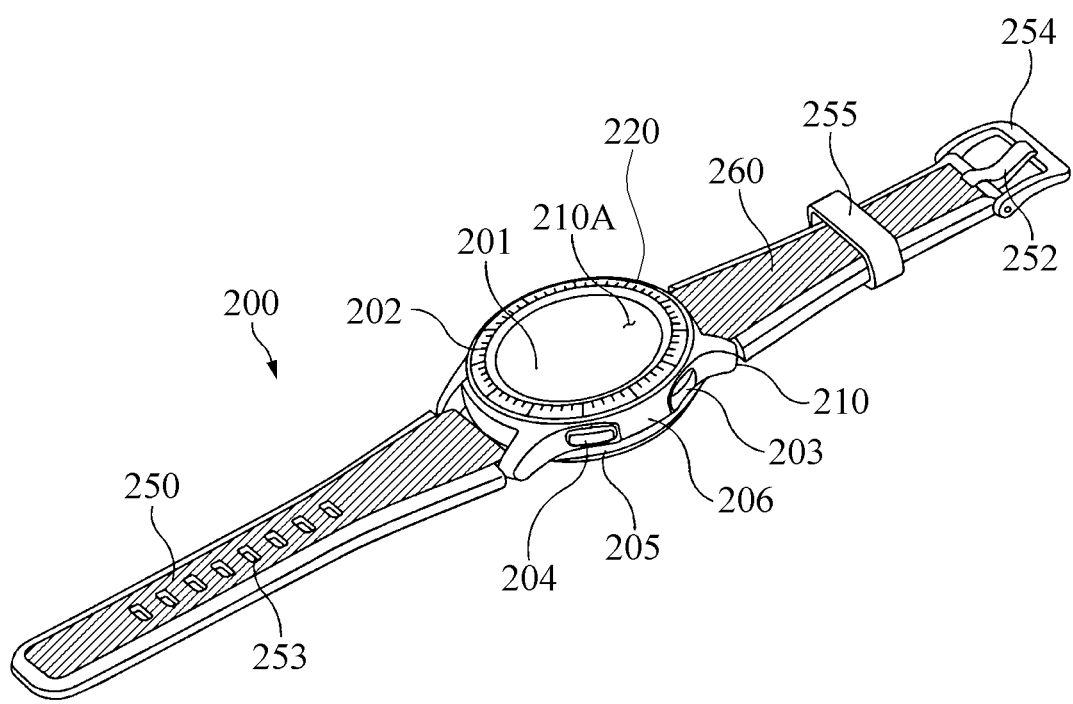
FIGS. 2A and 2B are perspective views of an portable device according to one embodiment.
Figure 2B:
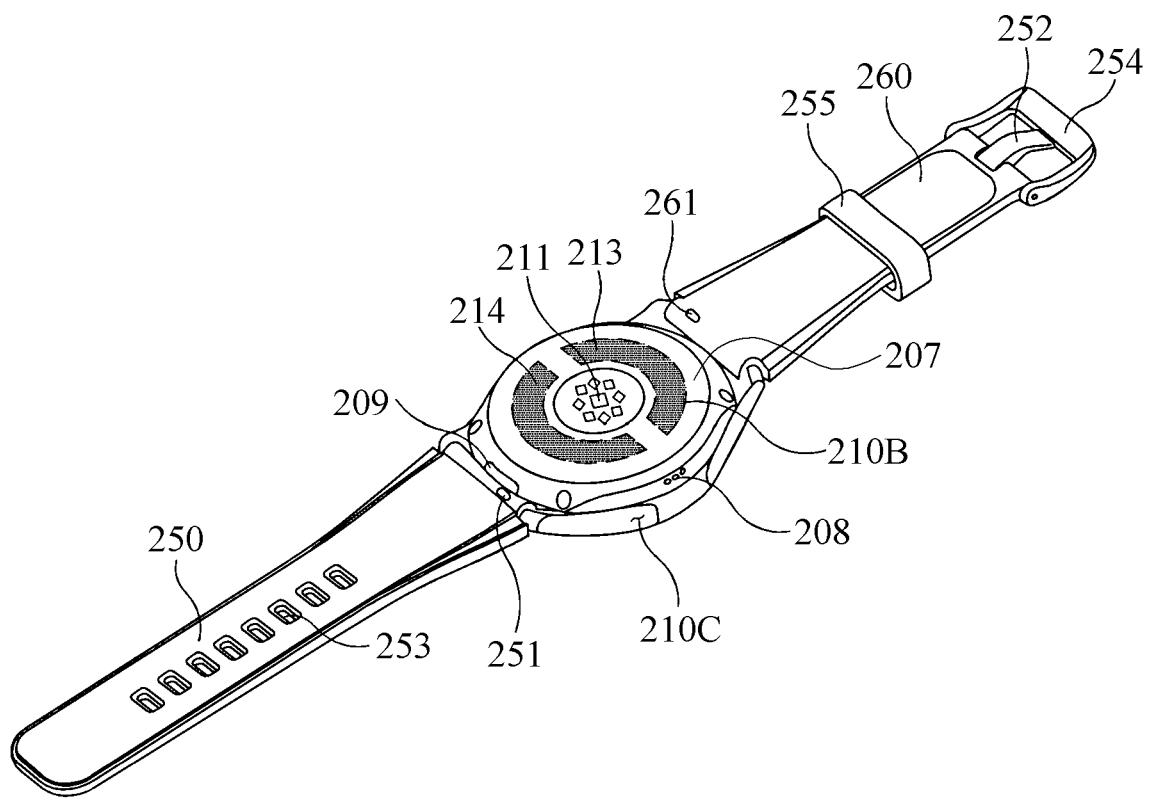

FIGS. 2A and 2B are perspective views of an portable device according to one embodiment. Referring to FIGS. 2A and 2B, according to an embodiment, a portable device 200 (e.g., the electronic device 101 of FIG. 1) may include a housing 210 including a first surface (or a front surface) 210A, a second surface (or a rear surface) 210B, and a side surface 210C surrounding a space between the first surface 210A and the second surface 210B, and fastening members 250 and 260 connected to at least a portion of the housing 210 and configured to detachably attach the portable device 200 to a body part (e.g., a wrist or an ankle) of a user. In an embodiment (not shown), the housing may also refer to a structure that forms a portion of the first surface 210A, the second surface 210B, and the side surface 210C of FIG. 2A. According to an embodiment, the first surface 210A may be formed by a front plate 201 (e.g., a glass plate or a polymer plate including various coating layers) of which at least a portion is substantially transparent. The second surface 210B may be formed by a rear plate 207 that is substantially opaque. The rear plate 207 may be formed of, for example, coated or colored glass, ceramic, polymer, metal (e.g., aluminum, stainless steel (SS), or magnesium), or a combination of at least two thereof. The side surface 210C may be coupled to the front plate 201 and the rear plate 207 and may be formed by a side bezel structure (or a "side member") 206 including a metal and/or a polymer. In an embodiment, the rear plate 207 and the side bezel structure 206 may be integrally formed and may include the same material (e.g., a metal material such as aluminum). The fastening members 250 and 260 may be formed of various materials and may have various shapes. For example, the fastening members 250 and 260 may be formed of woven fabric, leather, rubber, urethane, metal, ceramic, or a combination of at least two of the aforementioned materials and may be implemented in an integrated form or with a plurality of unit links that are movable relative to each other.

According to an embodiment, the portable device 200 may include at least one of a display 220 (e.g., the display module 160 of FIG. 1), audio modules 205 and 208 (e.g., the input module 150 or the sound output module 155 of FIG. 1), a sensor module 211 (e.g., the sensor module 176 of FIG. 1), key input devices 202, 203, and 204 (e.g., the input module 150 of FIG. 1), or a connector hole 209. In an embodiment, the portable device 200 may not include at least one (e.g., the key input devices 202, 203, and 204, the connector hole 209, or the sensor module 211) of the components, or additionally include other components.

The display 220 may be exposed through, for example, some portions of the front plate 201. The display 220 may have a shape corresponding to a shape of the front plate 201, and may have various shapes such as a circle, an oval, or a polygon. The display 220 may be coupled to or disposed adjacent to a touch sensing circuit, a pressure sensor capable of measuring an intensity (or pressure) of a touch, and/or a fingerprint sensor.

The audio modules 205 and 208 may include a microphone hole 205 and a speaker hole 208. A microphone for acquiring an external sound may be disposed in the microphone hole 205. In some embodiments, a plurality of microphones may be disposed to detect a direction of a sound. The speaker hole 208 may be used as an external speaker and a call receiver for calls. In an embodiment, the speaker hole 208 and the microphone hole 205 may be implemented as a single hole, or a speaker (e.g., a piezo speaker) may be included without the speaker hole 208.

The sensor module 211 may generate an electrical signal or a data value corresponding to an internal operating state of the portable device 200 or an external environmental state (e.g., a user state). The sensor module 211 may include, for example, a biometric sensor module 211 (e.g., a heart rate monitor (HRM) sensor) disposed on the second surface 210B of the housing 210. The portable device 200 may further include at least one of sensor modules (not shown), for example, a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor.

The sensor module 211 may include electrode areas 213 and 214 that form a portion of the surface of the portable device 200 and a biosignal detection circuit (not shown) electrically connected to the electrode areas 213 and 214. For example, the electrode areas 213 and 214 may include a first electrode area 213 and a second electrode area 214 disposed on the second surface 210B of the housing 210. The sensor module 211 may be configured such that the electrode areas 213 and 214 obtain electrical signals from a part of the user's body and the biosignal detection circuit detects biometric information of the user based on the electrical signals.

The key input devices 202, 203, and 204 may include a wheel key 202 disposed on the first surface 210A of the housing 210 and rotatable in at least one direction, and/or side key buttons 203 and 204 disposed on the side surface 210C of the housing 210. The wheel key 202 may have a shape corresponding to the shape of the front plate 201. In an embodiment, the portable device 200 may not include some or all of the above-described key input devices 202, 203, and 204, and the key input devices 202, 203, and 204 that are not included may be implemented in other forms such as soft keys on the display 220. The connector hole 209 may include another connector hole (not shown) that accommodates a connector (e.g., a universal serial bus (USB) connector) for transmitting and receiving power and/or data to and from an external electronic device and accommodates a connector for transmitting and receiving an audio signal to and from an external electronic device. The portable device 200 may further include, for example, a connector cover (not shown) that covers at least a portion of the connector hole 209 and blocks or reduces the infiltration of external foreign materials into the connector hole 209.

The fastening members 250 and 260 may be detachably fastened to at least a partial area of the housing 210 using locking members 251 and 261. The fastening members 250 and 260 may include one or more of a fixing member 252, a fixing member fastening hole 253, a band guide member 254, and a band fixing ring 255.

The fixing member 252 may be configured to fix the housing 210 and the fastening members 250 and 260 to a part (e.g., a wrist, an ankle, etc.) of the user's body. The fixing member fastening hole 253 may correspond to the fixing member 252 to fix the housing 210 and the fastening members 250 and 260 to the part of the user's body. The band guide member 254 may be configured to limit a range of a movement of the fixing member 252 when the fixing member 252 is fastened to the fixing member fastening hole 253, so that the fastening members 250 and 260 may be fastened to the part of the user's body in a state of being brought into close contact with the part of the user's body. The band fixing ring 255 may limit a range of a movement of the fastening member 250, 260 in a state in which the fixing member 252 and the fixing member fastening hole 253 are fastened with each other.

Figure 3:
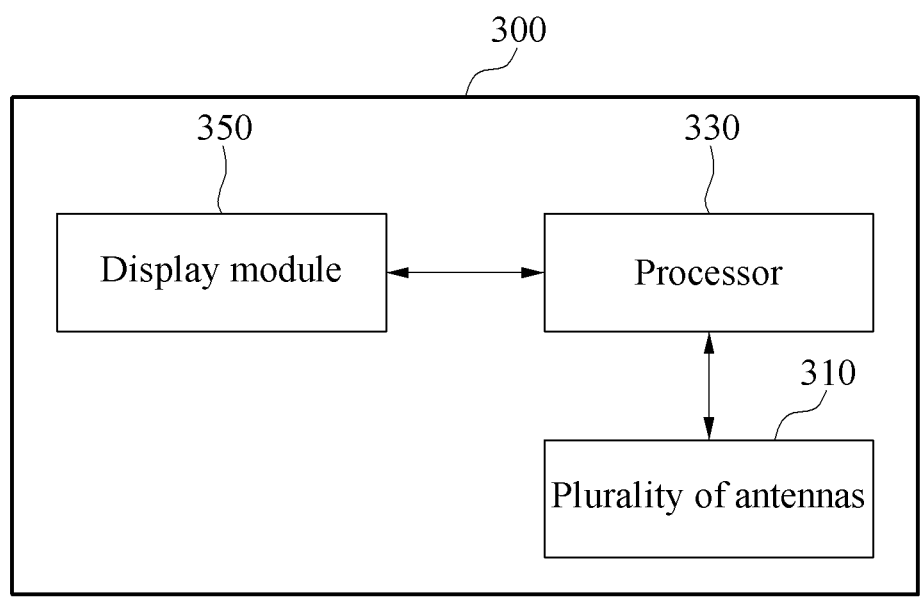
FIG. 3 is a block diagram illustrating an electronic device according to one embodiment.

FIG. 3 is a block diagram illustrating an electronic device according to one embodiment. Referring to FIG. 3, according to an embodiment, an electronic device 300 (e.g., the electronic device 102 of FIG. 1) may include a plurality of antennas 310, a processor 330, and a display module 350.

The electronic device 300 may display various images through the display module 350 (e.g., including a display). Here, the images may include still images and moving images, and the electronic device 300 may display various images such as broadcast content and multimedia content through the display module 350. Further, the electronic device 300 may display a user interface (UI) and an icon. The electronic device 300 may include, for example, a display device such as a smart TV or an Internet TV. However, embodiments are not limited thereto.

The plurality of antennas 310 (e.g., antennas 417 of FIG. 4) may wirelessly communicate with one or more portable devices (e.g., the electronic device 101 of FIG. 1 or the portable device 200 of FIGS. 2A and 2B) adjacent to the electronic device 300. For example, the plurality of antennas 310 may be disposed at both ends of a display panel (e.g., a display panel 412 of FIG. 4 and/or a display panel 620 of FIG. 6) of the display module 350 or on a bezel of a display panel 620. One or more of the plurality of antennas 310 may be disposed at each of two or more symmetrical positions among top, bottom, left, and right of the display module 350. The plurality of antennas 310 may be disposed, for example, one at each of symmetrical positions on the left and right of the display module 350 or one at each of symmetrical positions on the left, right, top, and bottom of the display module 350. Alternatively, at least one of the plurality of antennas 310 may be disposed at each of the left, right, top, and bottom of the display module 350. However, embodiments are not limited thereto.

The processor 330 (e.g., a processor 414 of FIG. 4) may scan whether there are one or more portable devices 200 using the plurality of antennas 310. According to an embodiment, the portable device 200 may include, for example, a smart phone, a tag-type device, a dedicated band, a band-type wearable device, a watch-type wearable device, and a glasses-type wearable device. However, embodiments are not limited thereto. Hereinafter, for ease of description, the operation of a watch-type wearable device, which is an example of a portable device, will be mainly described. However, the description may also apply to various other portable devices.

The processor 330 may scan signals received through the plurality of antennas 310, thereby searching for and/or recognizing one or more portable devices 200 adjacent to the electronic device 300. A method of searching for and/or recognizing one or more portable devices 200 by the processor 330 will be described further below with reference to FIG. 5.

The processor 330 may define a three-dimensional recognition space (e.g., a recognition space 630 of FIG. 6, a recognition space 740 of FIG. 7, a recognition space 830 of FIG. 8, a recognition space 850 of FIG. 8, and/or a recognition space 1340 of FIG. 13) based on a first signal transmitted from the portable device 200 for space setting. Here, the "recognition space" may refer, for example, to a three-dimensional virtual space representing a range within which the electronic device 300 may recognize the position of a user wearing the portable device 200. The processor 330 may define the recognition space 630 relative to a front side (e.g., a +z direction of FIG. 6) of the display module 350 based on the first signal. The front side of the display module 350 may refer, for example, more specifically, to a front side of the display panel (e.g., the display panel 412 of FIG. 4 and/or the display panel 620 of FIG. 6) included in the display module 350. In this case, the "front side" of the display panel may, for example, be the front side of a wireless signal space, or the front side of a space where a user consumes exercise content, that is, the front side of the display panel 620 corresponding to a space where a user exercises. According to an embodiment, when trainees view a projection screen that is separately connected to show a screen of a small electronic device that a personal trainer views, the front side of the display panel may be the front side of the projection screen or a space facing the projection screen.

Based on wireless signals, the front side may be recognized, for example, as the front side of the electronic device 300 on which the screen of the display panel 620 is displayed, or as the rear side of the electronic device 300. Since the front side and the rear side of the electronic device 300 may be recognized as the same by signals, the front side of the wireless signal space may be the front side of the electronic device 300 or the rear side of the electronic device 300. For example, the electronic device 300 may distinguish the front side of the wireless signal space, for example, by instructing to move left and right in front of the display panel 620, performing triangulation using the plurality of antennas 310, or turning on a camera.

In an embodiment, the "front side" of the display panel may be construed as the front side of the display panel 620 corresponding to a space where a user exercises. For example, the electronic device 300 may recognize the front side of the display panel 620 based on whether a user is captured through a camera, or recognize whether the portable device 200 is positioned on the front side of a space where a user consumes an exercise content through ultra-wideband (UWB) wireless signals based on the range of the recognition space 630 which will be described below.

In response to a space setting mode being started in the portable device 200 for setting the recognition space 630, the processor 330 may provide a user of the portable device 200 with a guide to guide the portable device 200 to be positioned in a boundary area of the recognition space 630 in which the exercise content is to be utilized. The processor 330 may set the plurality of antennas 310 to receive the first signal transmitted from the portable device 200 according to the guide. When each of the plurality of antennas 310 successfully receives the first signal transmitted from the portable device 200 in the boundary area of the recognition space 630 according to the guide, the processor 330 may provide a guide to guide the portable device 200 to move to a boundary area next to the boundary area.

When each of the plurality of antennas 310 successfully receives the first signal, the processor 330 may define the recognition space 630 using the first signal received by each of the plurality of antennas 310. The recognition space 630 according to an embodiment and a method of defining the recognition space 630 by the processor 330 will be described further below with reference to FIGS. 6, 7, and 8.

The processor 330 may calculate the position of the portable device 200 in the recognition space 630 based on a second signal transmitted from the portable device 200. In this case, the second signal transmitted from the portable device 200 may be the same as the first signal or different from the first signal. The processor 330 may calculate a first relative position including a distance and an angle between the electronic device 300 and the portable device 200 using a difference in times at which the plurality of antennas 310 receive the second signal. The processor 330 may identify whether the portable device 200 is positioned in the recognition space 630 based on the first relative position. For example, when it is identified that the portable device 200 is not positioned in the recognition space 630, the processor 330 may reconstruct the exercise content by deleting a character corresponding to the portable device 200 from the exercise content. Conversely, when it is identified that the portable device 200 is positioned in the recognition space 630, the processor 330 may determine whether identification information of the portable device 200 is or corresponds to pre-enrolled information, and reconstruct the exercise content with a character corresponding to the portable device 200 according to whether identification information is or corresponds to pre-enrolled information. A method of calculating the position of the portable device 200 based on the second signal by the processor 330 will be described further below with reference to FIGS. 9 and 10.

The processor 330 may generate exercise content based on the position of the portable device 200. The processor 330 may identify whether the portable device 200 leaves the recognition space 630 or newly enters the recognition space 630 while the display module 350 is displaying the exercise content, based on the second signal. For example, when it is identified based on the second signal that the portable device 200 leaves the recognition space 630, the processor 330 may remove a character corresponding to the leaving portable device 200 from the exercise content. Conversely, when it is identified based on the second signal that the portable device 200 newly enters the recognition space 630, the processor 330 may add a character corresponding to the newly entering portable device 200 to the exercise content. A method of generating the exercise content by the processor 330 will be described further below with reference to FIGS. 11, 12, 13, 14, 15, and 16.

The processor 330 (e.g., including processing circuitry) may control the overall operation of the electronic device 300. The processor 330 may include one or more processors. The processor 330 may include a plurality of processor modules (e.g., a first processor module and a second processor module), and each of the plurality of processor modules may partially and separately perform any data operation or data processing. Specifically, the processor 330 may perform or control the operation of the electronic device 300 by executing at least one instruction stored in a memory (not shown).

In addition, the processor 330 may perform at least one method that will be described with reference to FIGS. 4 through 17 below or a scheme corresponding to the at least one method. The electronic device 300 may be one in which the processor 330 is implemented as hardware having a circuit that is physically structured to execute desired operations. For example, the desired operations may include code or instructions included in a program. The hardware-implemented processor 330 may include, for example, a microprocessor, a central processing unit (CPU), a graphics processing unit (GPU), a processor core, a multi-core processor, a multiprocessor, an application-specific integrated circuit (ASIC), a field-programmable gate array (FPGA), and/or a neural processing unit (NPU). Alternatively, the processor 330 may be implemented as a digital signal processor (DSP) that processes a digital image signal, an artificial intelligence (AI) processor, or a time controller (TCON). However, embodiments are not limited thereto, and the processor 330 may include one or more of a CPU, a micro controller unit (MCU), a micro processing unit (MPU), a controller, an application processor (AP), a communication processor (CP), or an ARM processor, or may be defined by a corresponding term. Further, the processor 330 may be implemented as a system on chip (SoC) with a processing algorithm embedded or a large scale integration (LSI), or implemented in the form of an ASIC or FPGA.

The processor 330 may drive an operating system or an application program to control hardware or software components connected to the processor 330 and perform various data processing or computation. In addition, the processor 330 may load instructions or data received from at least one of the other components to a memory (not shown) to process the same, and store a variety of data in a non-volatile memory (not shown).

Figure 14:
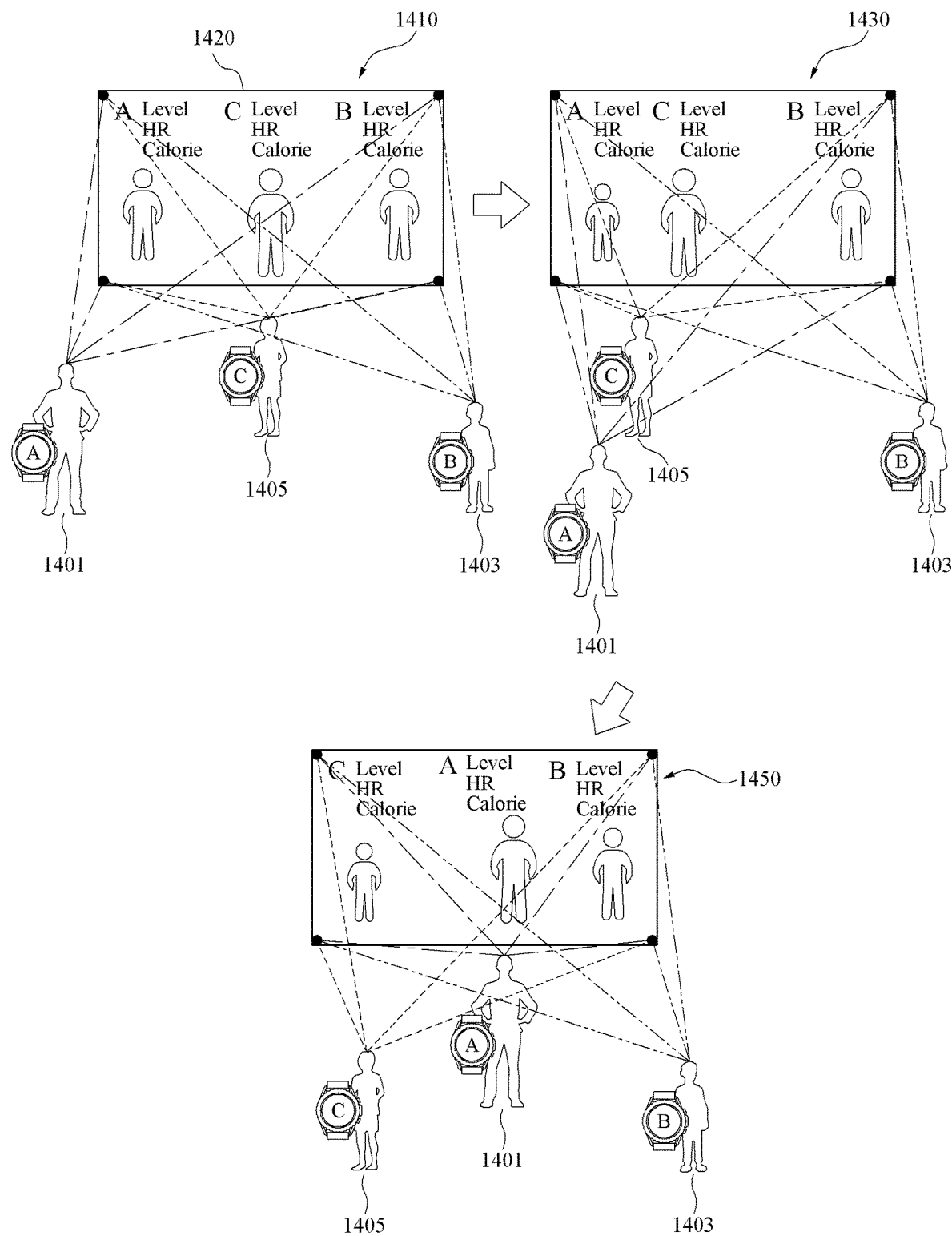
FIG. 14 is a diagram illustrating an method of reconstructing an exercise content in response to changes in the positions of portable devices positioned in a recognition space according to one embodiment.
Figure 15:
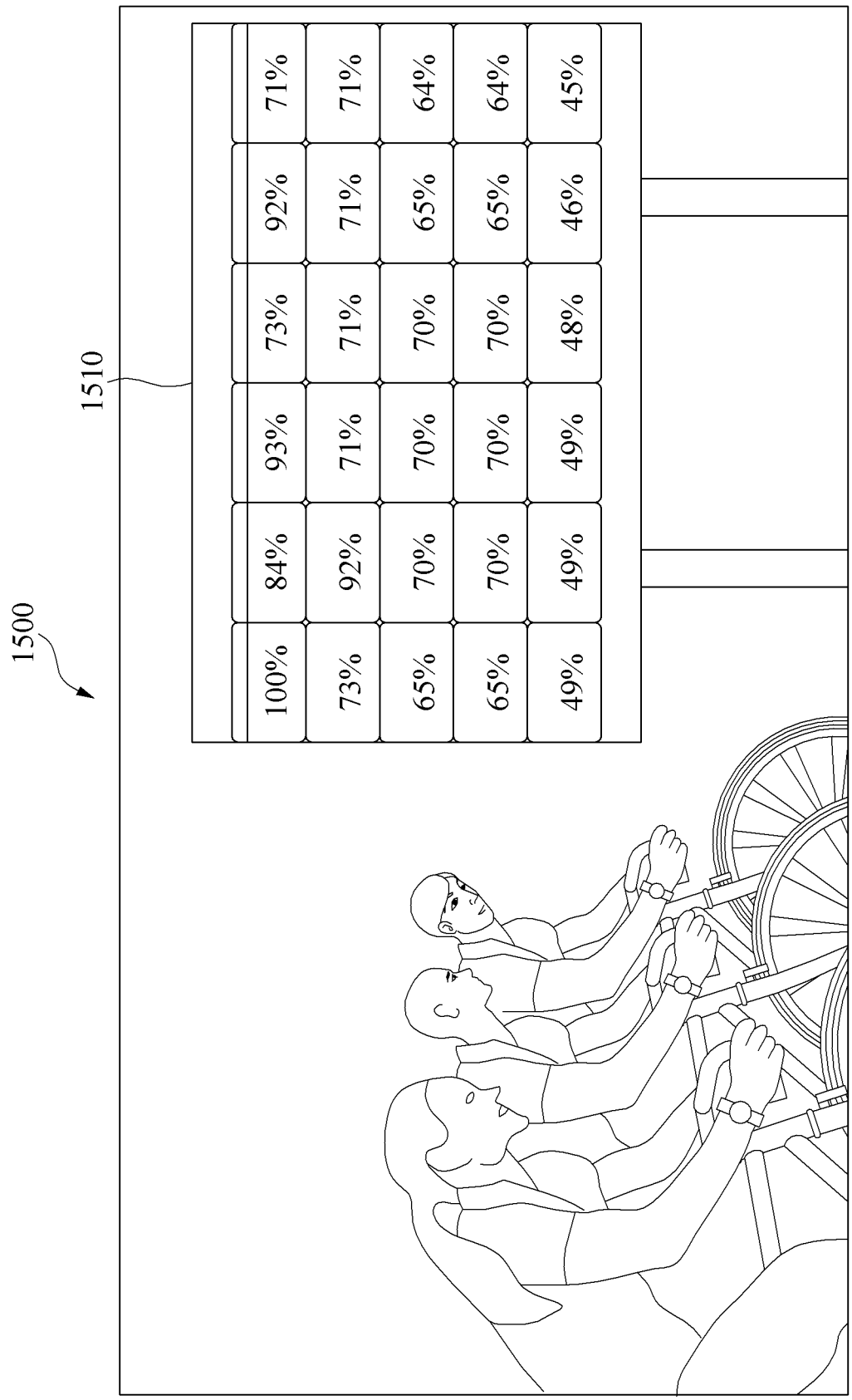
FIG. 15 is a diagram illustrating an example of displaying the positions of a plurality of users in an exercise content when the plurality of users perform a group exercise wearing portable devices according to one embodiment.
Figure 16:
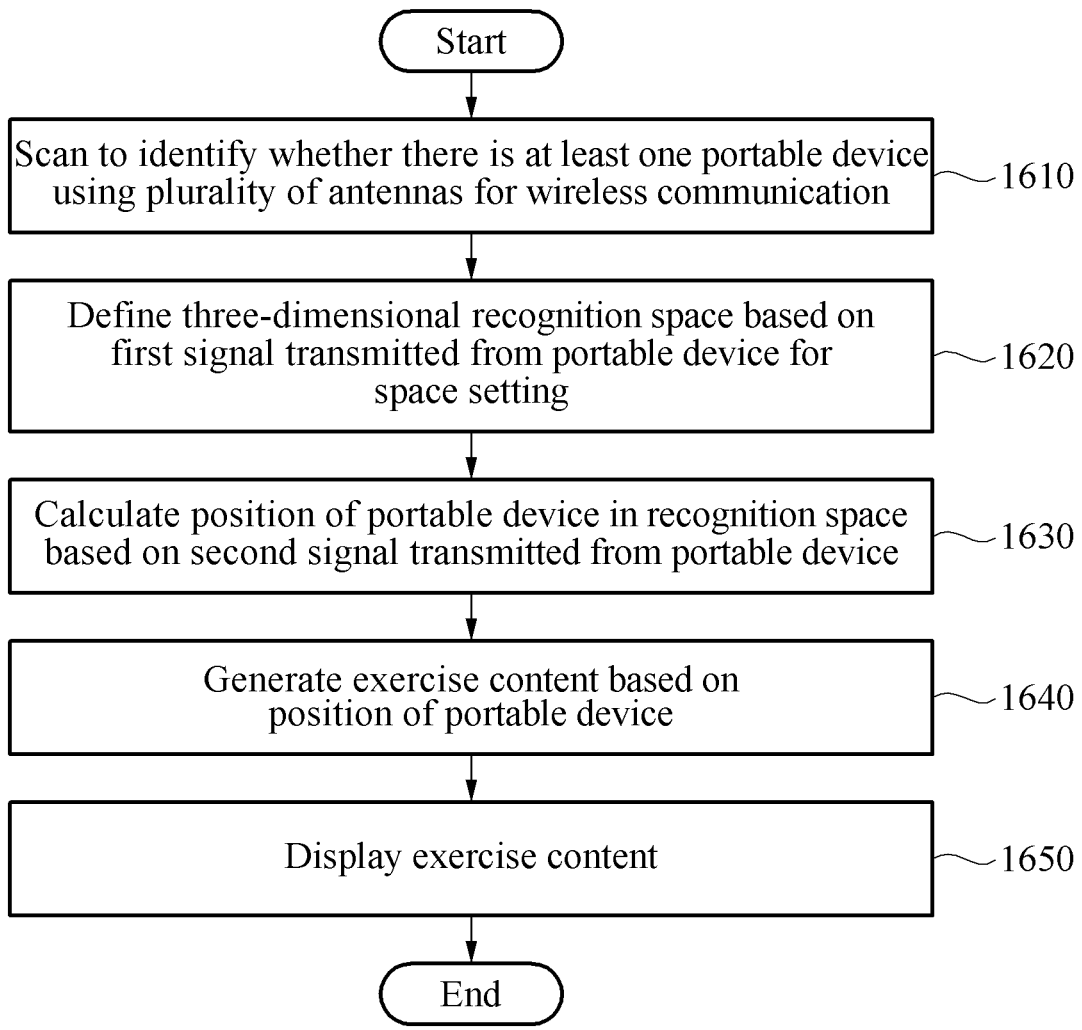
FIG. 16 is a flowchart illustrating an operating method of an electronic device according to one embodiment.

The display module 350 (e.g., including a display) may display exercise content generated by the processor 330. In this case, the exercise content may include, for example, a dance content and a group exercise content. As shown in FIGS. 14, 15, and 16, the exercise content may include, for example, at least one of a character corresponding to a user wearing the portable device 200 or exercise information of the user wearing the portable device 200. The character corresponding to the user wearing the portable device 200 may be, for example, an avatar of the user or an emoji. However, embodiments are not limited thereto. The character may be selected by the user from among various characters provided by the processor 330 to the user or arbitrarily set by the processor 330. The exercise information of the user may include, for example, biometric information of the user (e.g., the body temperature, the heart rate, and/or the consumed calories of the user) sensed through the portable device 200 while the user performs various exercises such as dancing, spinning, yoga, or fitness according to the exercise content displayed through the display module 350 of the electronic device 300. However, embodiments are not limited thereto.

More specifically, the display module 350 may include an integrated circuit (IC) chip (not shown), and the IC chip may display an image based on an image signal received from the processor 330. For example, the IC chip may display the image by generating driving signals of a plurality of light sources based on the image signal received from the processor 330 and controlling light emitted from a plurality of pixels (not shown) included in the display module 350 based on the driving signals.

The display module 350 may include a driving circuit that may be implemented in the form of an a-si thin film transistor (TFT), a low temperature poly silicon (LTPS) TFT, or an organic TFT (OTFT), and a backlight unit.

According to an embodiment, the display module 350 may be implemented as various types of displays, such as a liquid crystal display (LCD), a quantum dot (QD) display panel, an organic light-emitting diode (OLED), a liquid crystal on silicon (LCoS), a digital light processing (DLP), a quantum dot light-emitting diode (QLED), a micro light-emitting diode (μLED), or a mini LED. Meanwhile, the display module 350 may be implemented as a touch screen combined with a touch sensor, a flexible display, a rollable display, a three-dimensional (3D) display, or a display in which a plurality of display modules are physically connected.

Figure 4:
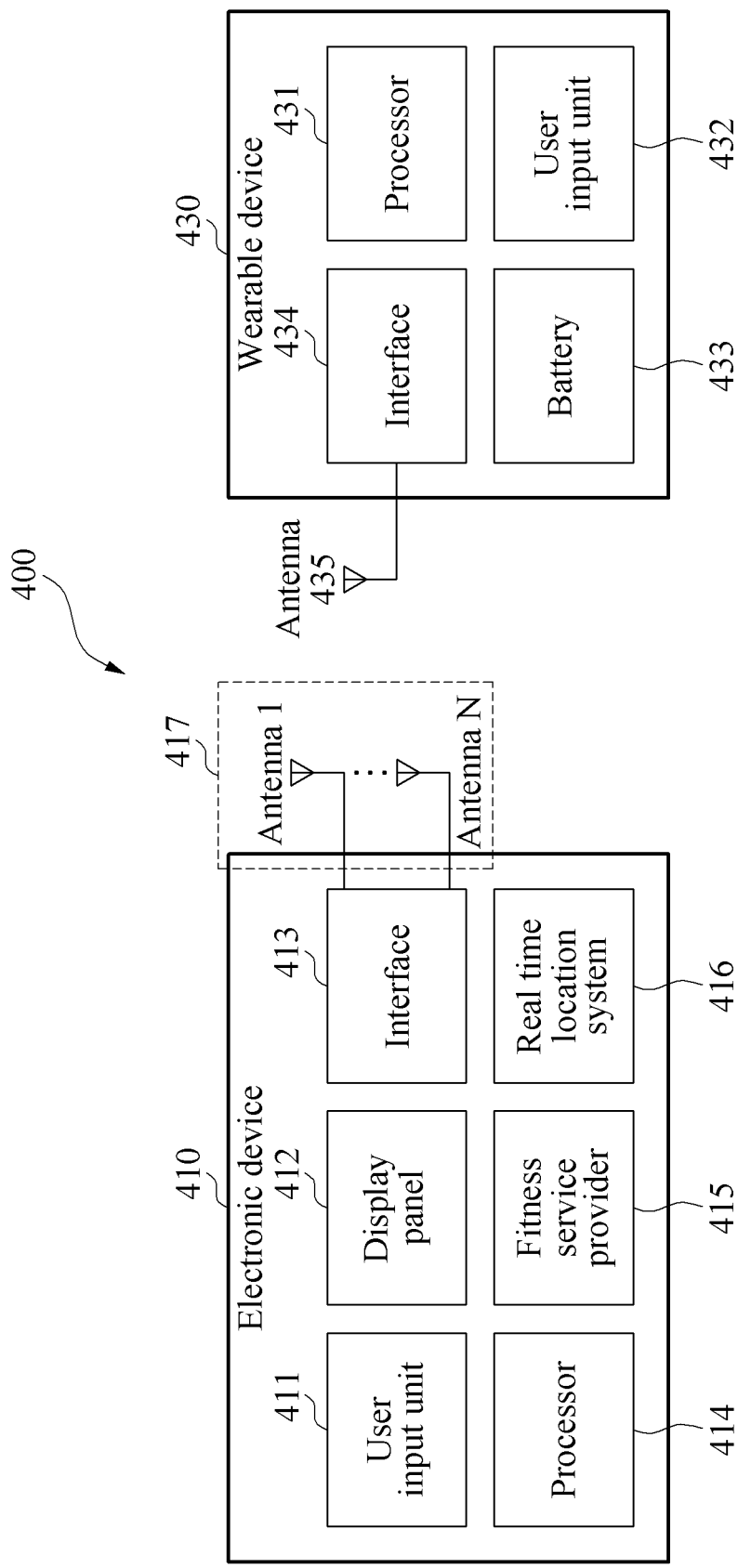
FIG. 4 is a block diagram of an system for providing an exercise content according to one embodiment.

FIG. 4 is a block diagram of an system for providing an exercise content according to one embodiment. Referring to FIG. 4, according to an embodiment, a system 400 may include an electronic device 410 (e.g., the electronic device 102 of FIG. 1, the electronic device 300 of FIG. 3, an electronic device 510 of FIG. 5, an electronic device 710 of FIG. 7, an electronic device 810 of FIG. 8, an electronic device 910 of FIG. 9, an electronic device 1001 of FIG. 10, an electronic device 1220 of FIG. 12, an electronic device 1320 of FIG. 13, an electronic device 1420 of FIG. 14, and/or an electronic device 1510 of FIG. 15), and a wearable device 430 (e.g., the electronic device 101 of FIG. 1, the portable device 200 of FIGS. 2A and 2B, a portable device 720 of FIG. 7, a portable device 820 of FIG. 8, a portable device 930 of FIG. 9, a portable device 1003 of FIG. 10, portable devices 1201, 1203, and 1205 of FIG. 12, portable devices 1301 and 1303 of FIG. 13, and/or portable devices 1401, 1403, and 1405 of FIG. 14).

Figure 9:
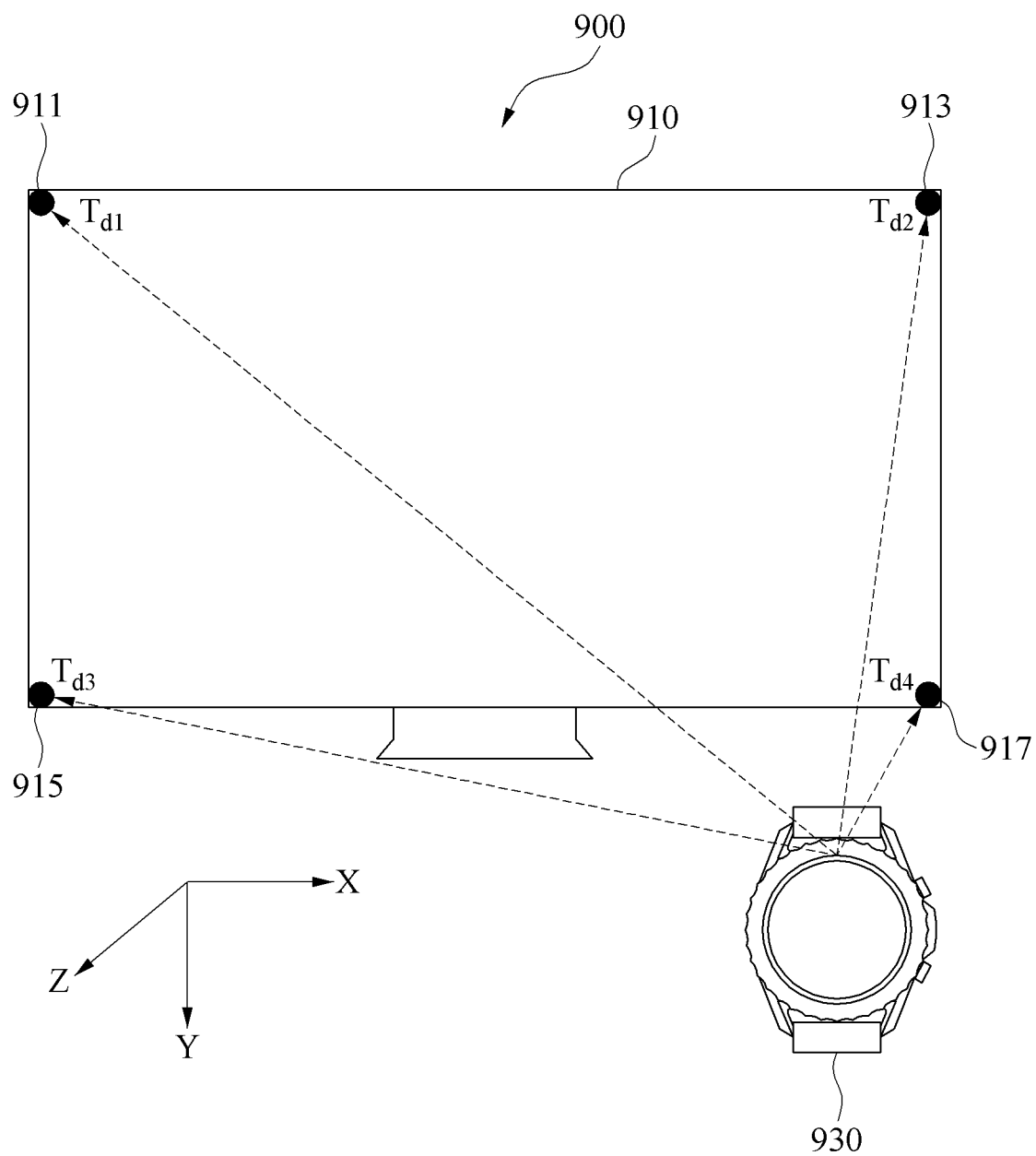
FIG. 9 is a diagram illustrating a method of calculating, by an electronic device, positions of portable devices based on second signals transmitted from the portable devices according to one embodiment.

The electronic device 410 may include a user input unit 411, a display panel 412 (e.g., the display panel 620 of FIG. 6), an interface 413, a processor 414 (e.g., the processor 330 of FIG. 3), a fitness service provider 415, a real time location system (RTLS) 416, and antennas 417 including antenna 1 through antenna N (e.g., the plurality of antennas 310 of FIG. 3, and/or a plurality of antennas 911, 913, 915, and 917 of FIG. 9).

The electronic device 410 may be, for example, a device including the display panel 412 on which the antennas 417 are mounted. However, embodiments are not limited thereto. The antennas 417 may be disposed, for example, one at each of symmetrical positions on the left and right of the display panel 412 or one at each of symmetrical positions on the left, right, top, and bottom of the display panel 412. In addition, at least one of the antennas 417 may be disposed at each of the left, right, top, and bottom of the display panel 412. However, embodiments are not limited thereto. The antennas 417 mounted at each position of the display panel 412 may receive a signal transmitted by the wearable device 430. The position of the wearable device 430 or the position of the user wearing the wearable device 430 may be measured based on a difference between the times at which the antennas 417 receive the signal.

The user input unit 411 (e.g., including circuitry) may receive an input of a user on contents displayed on the display panel 412 of the electronic device 410. The user input unit 411 may be, for example, a device for receiving various user inputs, such as a voice input, a camera input, a keyboard input, and/or a pen input, a dedicated controller, and/or a remote control. However, embodiments are not limited thereto.

The display panel 412 (e.g., including a display) may display exercise content including fitness content provided through the fitness service provider 415.

The interface 413 may, for example, including communication circuitry to provide connectivity with devices (e.g., portable devices) connected to the electronic device 410. The connectivity may be a wireless communication scheme that is the same as a connectivity of the portable device without specifying the specification of the electronic device 410, and may be, for example, any communication scheme capable of a time difference of arrival (TDoA) method. The connectivity may include, for example, Bluetooth communication, Bluetooth low energy (BLE) communication, Wi-Fi (WiFi) communication, near field communication (NFC), and/or ultra-wideband (UWB) communication. However, embodiments are not necessarily limited thereto.

The electronic device 410 may, for example, include a full-time power supply and have low mobility and thus, may be advantageous in a scanning operation rather than a broadcasting operation. In addition, since the electronic device 410 may be relatively large compared to mobile devices, a large UWB antenna may be disposed thereon. Thus, the electronic device 410 may be advantageous in determining the directional resolution of another device.

The processor 414 (e.g, including processing circuitry) may scan whether there is at least one wearable device 430 using the antennas 417, and define a three-dimensional recognition space (e.g., the recognition space 630 of FIG. 6, the recognition space 740 of FIG. 7, the recognition space 830 of FIG. 8, the recognition space 850 of FIG. 8, and/or the recognition space 1340 of FIG. 13) based on a first signal transmitted from the wearable device 430 for space setting.

The fitness service provider 415 may generate and/or provide exercise content for a fitness service based on the position of the wearable device 430 calculated by the RTLS 416. For example, when the calculated position of the wearable device 430 corresponds to the right side of the recognition space 630, the fitness service provider 415 may generate exercise content displaying a character corresponding to the wearable device 430 on the right side of the scene. As another example, when the calculated position of the wearable device 430 corresponds to the middle of the three-dimensional recognition space 630, the fitness service provider 415 may generate exercise content displaying a character corresponding to the wearable device 430 in the middle of the scene. As described above, the fitness service provider 415 may provide exercise content displaying a character reflecting the position of the wearable device 430 calculated by the RTLS 416, thereby providing exercise content reflecting a movement of a user in real time. In addition, the fitness service provider 415 may provide, for example, a service provided by an application executed by the processor 414 and/or a service provided by a server to which the wearable device 430 is connected.

The RTLS 416 may calculate the position of the wearable device 430 in the recognition space 630 by collecting a signal (e.g., a second signal) received by each of the N antennas 417 from the wearable device 430. The RTLS 416 may include various circuitry such as a clock used by the processor 414 to determine differences in arrival time of signals received by the antennas 417.

The antennas 417 may be for wireless communication with the wearable device 430. The antennas 417 may be disposed between the display panel 412 and a support member (not shown). The antennas 417 may include antennas for various wireless communication methods, for example, a Bluetooth antenna, a Wi-Fi antenna, an infrared data association (IrDA) antenna, a legacy cellular antenna, a 5G antenna, a near field communication (NFC) antenna, a wireless charging antenna, and/or a magnetic secure transmission (MST) antenna. However, embodiments are not limited thereto. For example, the antennas 417 may perform short-range communication with an external device, wirelessly transmit and receive power used for charging, or transmit a magnetism-based signal including a short-range communication signal or payment data.

According to an embodiment, when the electronic device 410 performs a predetermined function, multiple wireless connections may be provided in a complex and sequential manner. In this case, for example, according to current consumption and usability, a Bluetooth communication antenna may be primarily used, and a UWB antenna may be secondarily used.

In an embodiment, an antenna structure may be formed by a portion of a side bezel structure and/or the support member, or a combination thereof.

The wearable device 430 may include a processor 431 (e.g., including processing circuitry), a user input unit 432 (e.g., including circuitry), a battery 433 (e.g., the battery 189 of FIG. 1), an interface 434 (e.g., the communication module 190 of FIG. 1), and an antenna 435 (e.g., the antenna module 197 of FIG. 1).

In response to an input being received through the user input unit 432 (e.g., an input to a "Set" button), the processor 431 may control to transmit a signal including device information of the wearable device 430 and/or information on the position of the wearable device 430 in which the Set button is input to the electronic device 410.

The user input unit 432 may receive the input on the "Set" button from the user who has moved to the boundary area of the recognition space 630 according to a guide provided through the wearable device 430, which is set to be in the mode for space setting, and transmit the input to the processor 431.

The battery 433, which is a device for supplying power to at least one component of the wearable device 430, may include, for example, a primary cell that is not rechargeable, a secondary cell that is rechargeable, or a fuel cell. For example, at least a portion of the battery 433 may be disposed on substantially the same plane as a printed circuit board. The battery 433 may be integrally disposed inside the wearable device 430, or disposed detachably from the wearable device 430.

The interface 434 may including communication circuitry to provide connectivity with devices (e.g., the electronic device 410) connected to the wearable device 430. The connectivity may be a wireless communication scheme that is the same as the connectivity of the electronic device 410 without specifying the specification of the wearable device 430, and may be, for example, any communication scheme capable of the TDoA method. The connectivity may include, for example, Bluetooth communication, Bluetooth low energy (BLE) communication, Wi-Fi (WiFi) communication, near field communication (NFC), and/or ultra-wideband (UWB) communication. However, embodiments are not necessarily limited thereto.

The antenna 435 may be disposed between a printed circuit board (not shown) and a rear plate (not shown) (e.g., the rear plate 207 of FIG. 2B). However, embodiments are not limited thereto. The antenna 435 may include antennas for various wireless communication methods, for example, a Bluetooth antenna, a Wi-Fi antenna, an infrared data association (IrDA) antenna, a legacy cellular antenna, a 5G antenna, a near field communication (NFC) antenna, a wireless charging antenna, and/or a magnetic secure transmission (MST) antenna. However, embodiments are not limited thereto. For example, the antenna 435 may perform short-range communication with the electronic device 410, wirelessly transmit and receive power used for charging, or transmit a magnetism-based signal including a short-range communication signal. In an embodiment, an antenna structure may be formed by a portion of a side bezel structure (not shown) (e.g., the side bezel structure 206 of FIG. 2A) and/or the rear plate (not shown) (e.g., the rear plate 207 of FIG. 2B), or a combination thereof.

Figure 5:
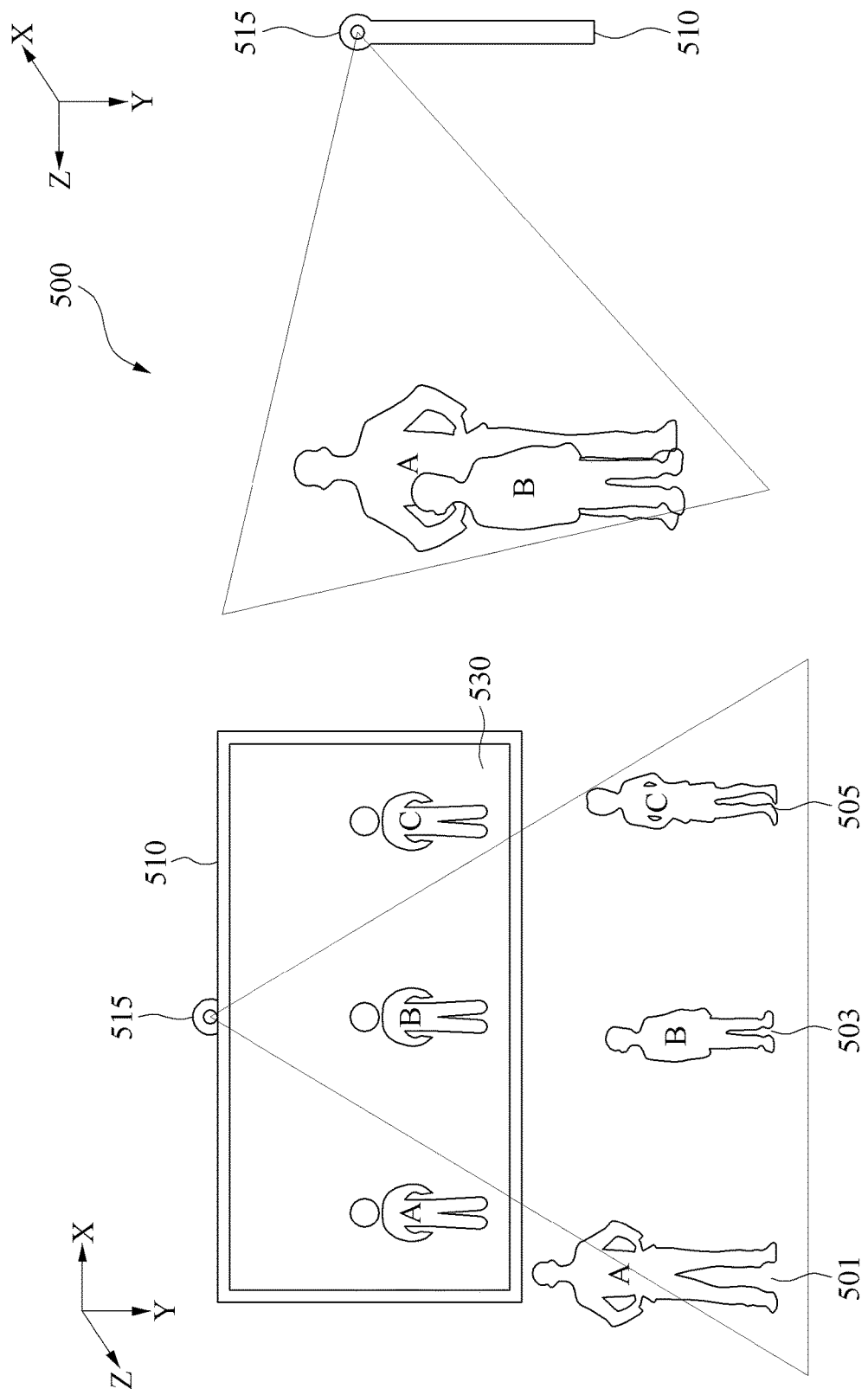
FIG. 5 is a diagram illustrating an operation of an electronic device according to one embodiment.

FIG. 5 is a diagram illustrating an operation of an electronic device according to one embodiment. Referring to FIG. 5, according to an embodiment, a diagram 500 illustrating a situation in which three users 501, 503, and 505 wearing portable devices (e.g., the electronic device 101 of FIG. 1, the portable device 200 of FIGS. 2A and 2B, the wearable device 430 of FIG. 4, the portable device 720 of FIG. 7, the portable device 820 of FIG. 8, the portable device 930 of FIG. 9, the portable device 1003 of FIG. 10, the portable devices 1201, 1203, and 1205 of FIG. 12, the portable devices 1301 and 1303 of FIG. 13, and/or the portable devices 1401, 1403, and 1405 of FIG. 14) are captured through a camera 515 disposed in a front side (e.g., the +z direction of FIG. 6) of a display panel (e.g., the display panel 412 of FIG. 4 and/or the display panel 620 of FIG. 6) of the electronic device 510 (e.g., the electronic device 102 of FIG. 1, the electronic device 300 of FIG. 3, the electronic device 410 of FIG. 4, the electronic device 710 of FIG. 7, the electronic device 810 of FIG. 8, the electronic device 910 of FIG. 9, the electronic device 1001 of FIG. 10, the electronic device 1220 of FIG. 12, the electronic device 1320 of FIG. 13, the electronic device 1420 of FIG. 14, and/or the electronic device 1510 of FIG. 15) is shown.

For example, the electronic device 510 may perform position recognition between devices of a wireless connection solution through a display module (e.g., the display module 350 of FIG. 3) and a processor (e.g., the processor 330 of FIG. 3) supporting wireless connection such as ultra wideband (UWB), thereby recognizing a plurality of users (e.g., users A, B, and C), tracking the positions of the plurality of users, and/or providing intuitive exercise content 530 according to relative positions between the electronic device 510 and the portable devices (e.g, portable devices 1003). Here, the "intuitive" exercise content 530 may refer, for example, to exercise content displaying characters respectively corresponding to the plurality of users so that the positions of the plurality of users wearing the portable devices in a recognition space (e.g., the recognition space 630 of FIG. 6, the recognition space 740 of FIG. 7, the recognition space 830 of FIG. 8, the recognition space 850 of FIG. 8, and/or the recognition space 1340 of FIG. 13) in the front side (e.g., the +z direction of FIG. 6) of the display panel 620 of the electronic device 510 may be immediately verified.

When the users approach the electronic device 510 in the front side (e.g., in the +z direction in FIG. 6) of the display panel 620, the electronic device 510 may recognize the positions of the portable devices (e.g., portable devices 1003) that the users are wearing and at the same time identify the plurality of users, thereby improving the use accessibility of each user to the exercise content.

The electronic device 510 may track the positions of the plurality of users positioned in the front side (e.g., in the +z direction of FIG. 6) of the display panel 620 and wearing the portable devices (e.g., portable devices 1003). Hereinafter, the "positions of the plurality of users" refers to the respective positions of the users wearing the portable devices 1003 and may, for example, refer to the positions of the portable devices 1003.

For example, the electronic device 510 may track an absolute position between the display panel 620 and the portable devices (e.g., portable devices 1003) and a relative position between the portable devices 1003. When the portable devices move to new positions as the plurality of users move, the electronic device 510 may reconstruct or update the exercise content to reflect the new positions. In addition, when a user positioned in the front side (e.g., the +z direction) of the display panel 620 moves and leaves the recognition space 630 and/or when a user newly enters the recognition space 630 from the outside, the electronic device 510 may display, in the exercise content, characters moved based on the new positions of the plurality of users to intuitively represent whether the users move, thereby improving the usability and the immersion of the users with respect to the recognition space 630.

Figure 6:
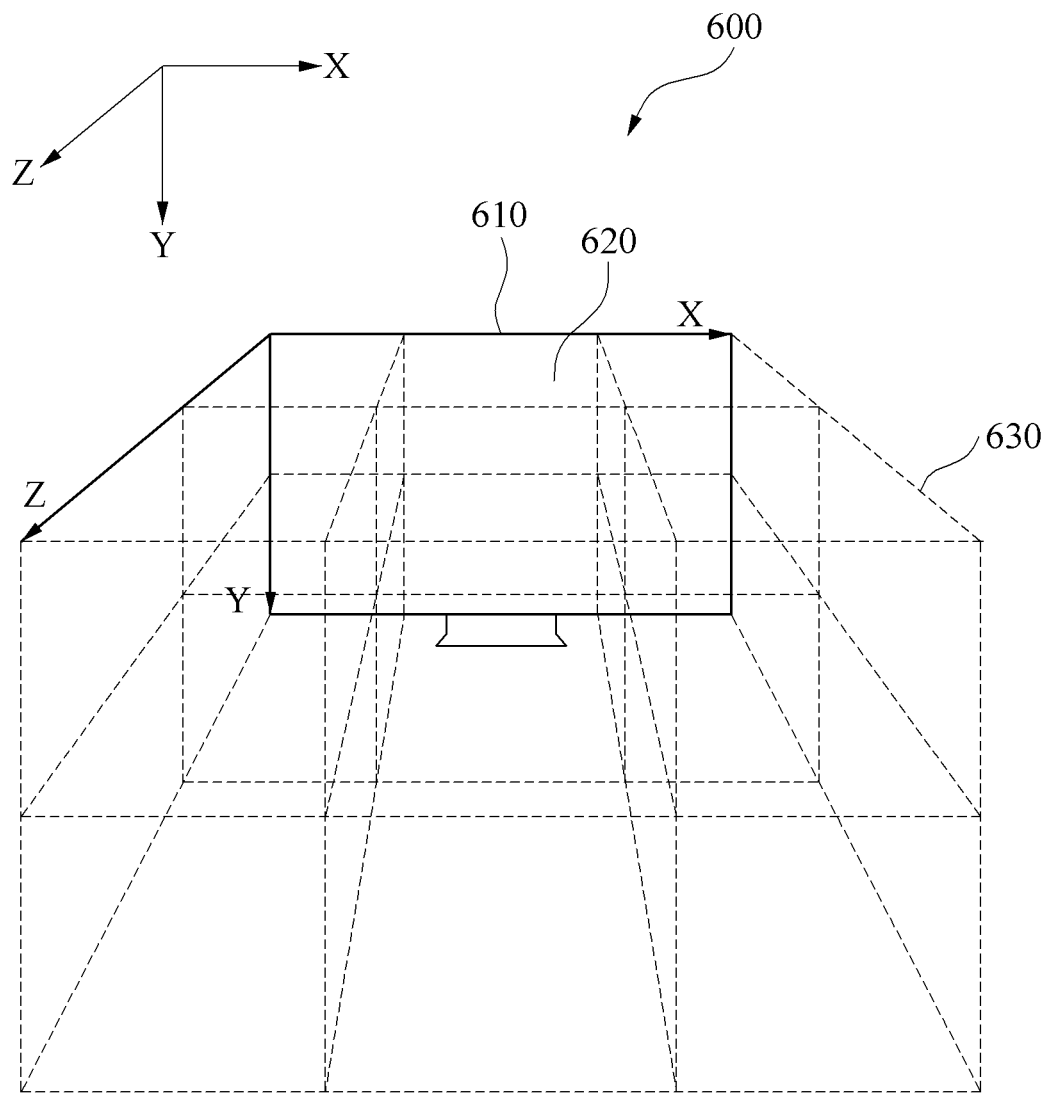
FIG. 6 is a diagram illustrating an example of a range of a recognition space in which an electronic device may recognize a position of a user wearing a portable device according to one embodiment.

FIG. 6 is a diagram illustrating an example of a range of a recognition space in which an electronic device may recognize a position of a user wearing a portable device according to one embodiment. Referring to FIG. 6, according to an embodiment, a diagram 600 illustrating an example of the recognition space 630 (e.g., the recognition space 740 of FIG. 7, the recognition space 830 of FIG. 8, the recognition space 850 of FIG. 8, and/or the recognition space 1340 of FIG. 13) set based on a front side (e.g., the +z direction of FIG. 6) of an electronic device 610 (e.g., the electronic device 102 of FIG. 1, the electronic device 300 of FIG. 3, the electronic device 410 of FIG. 4, the electronic device 510 of FIG. 5, the electronic device 710 of FIG. 7, the electronic device 810 of FIG. 8, the electronic device 910 of FIG. 9, the electronic device 1001 of FIG. 10, the electronic device 1220 of FIG. 12, the electronic device 1320 of FIG. 13, the electronic device 1420 of FIG. 14, and/or the electronic device 1510 of FIG. 15) is shown.

Figure 7:
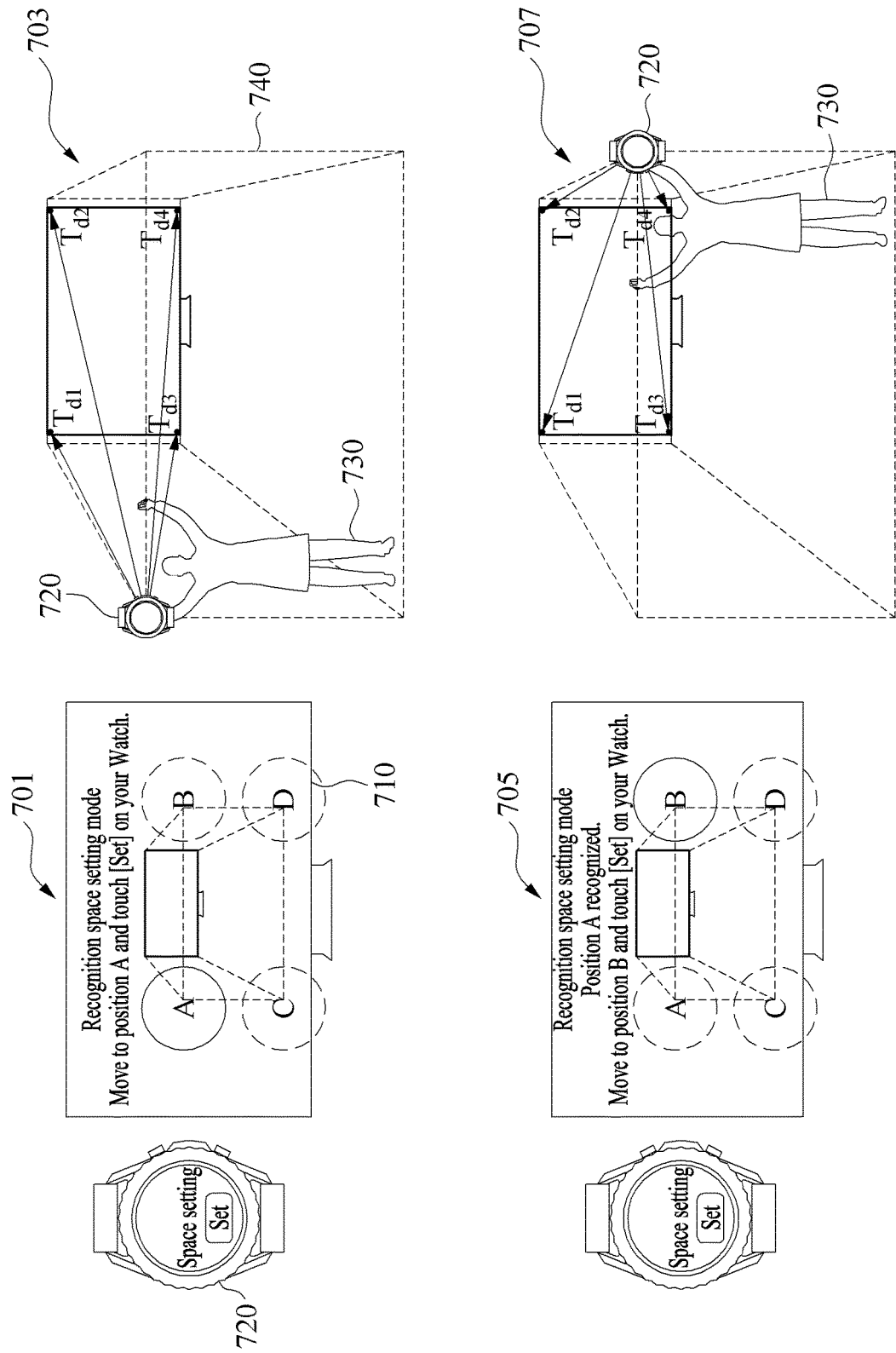
FIG. 7 is a diagram illustrating a method of defining a three-dimensional recognition space by an electronic device according to one embodiment.
Figure 8:
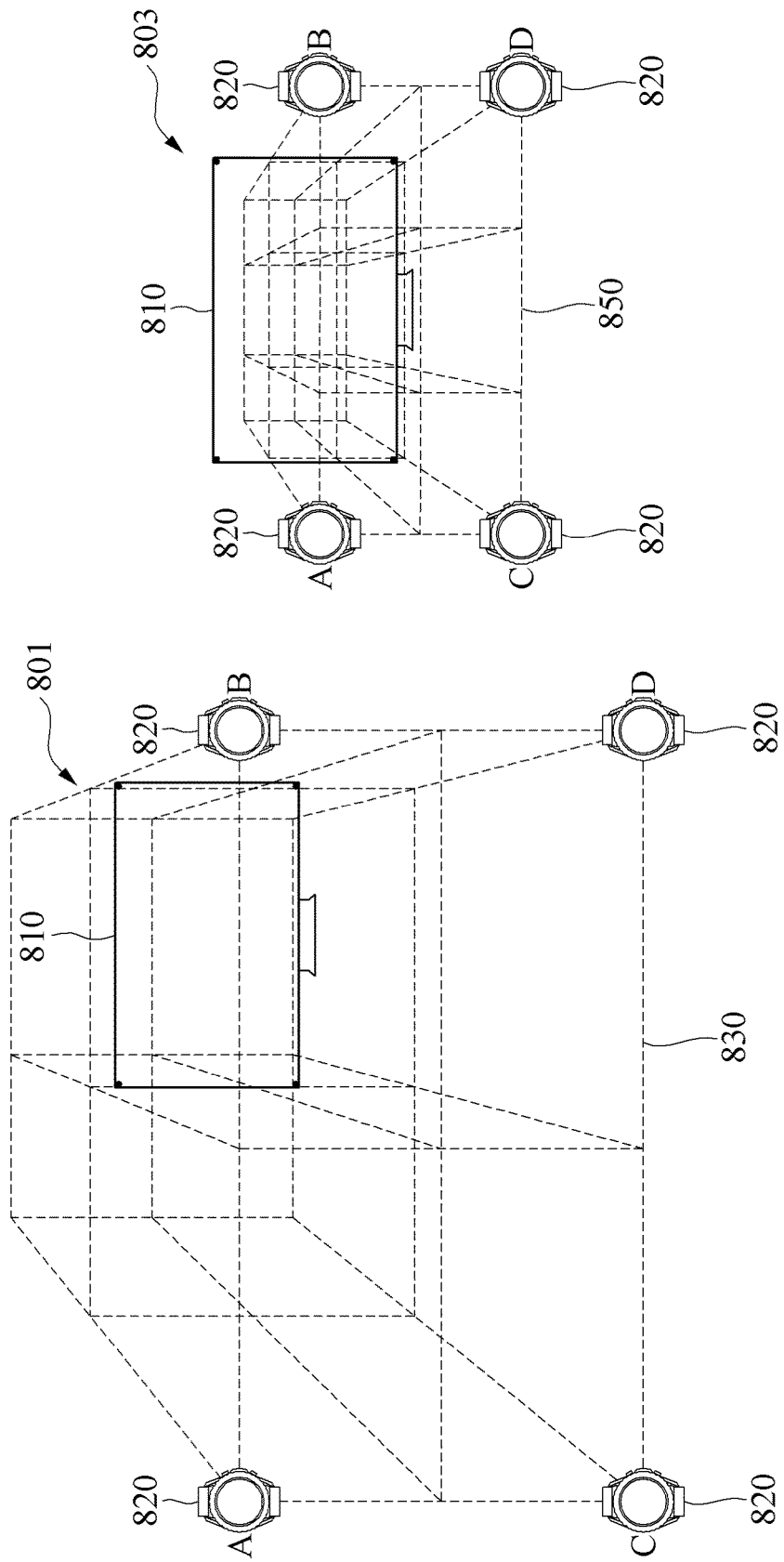
FIG. 8 is a diagram illustrating examples of a recognition space defined by an electronic device based on first signals transmitted from portable devices according to one embodiment.
Figure 10:
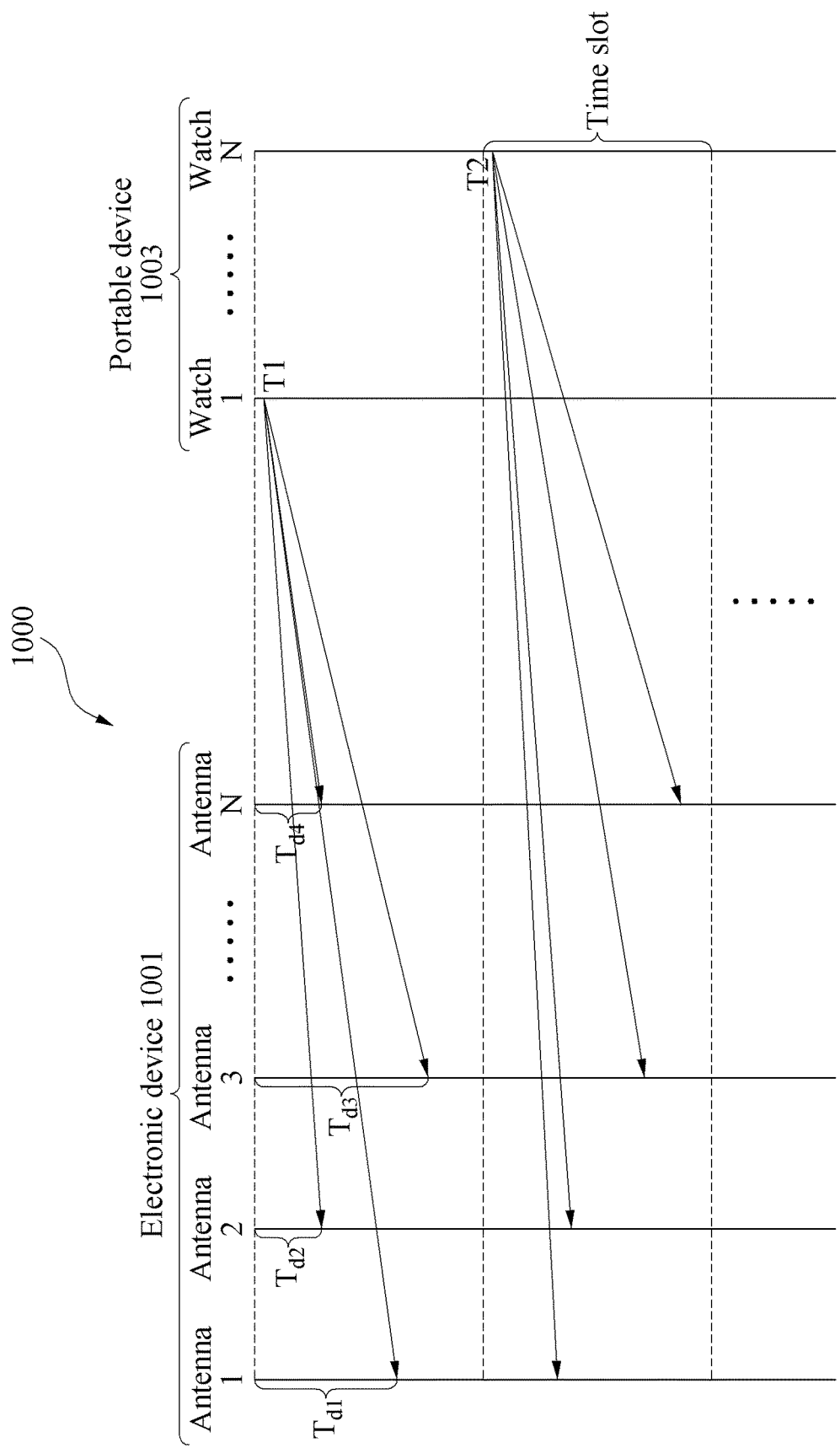
FIG. 10 is a diagram illustrating transmission and reception sequences between a plurality of antennas of an electronic device and portable devices according to one embodiment.
Figure 12:
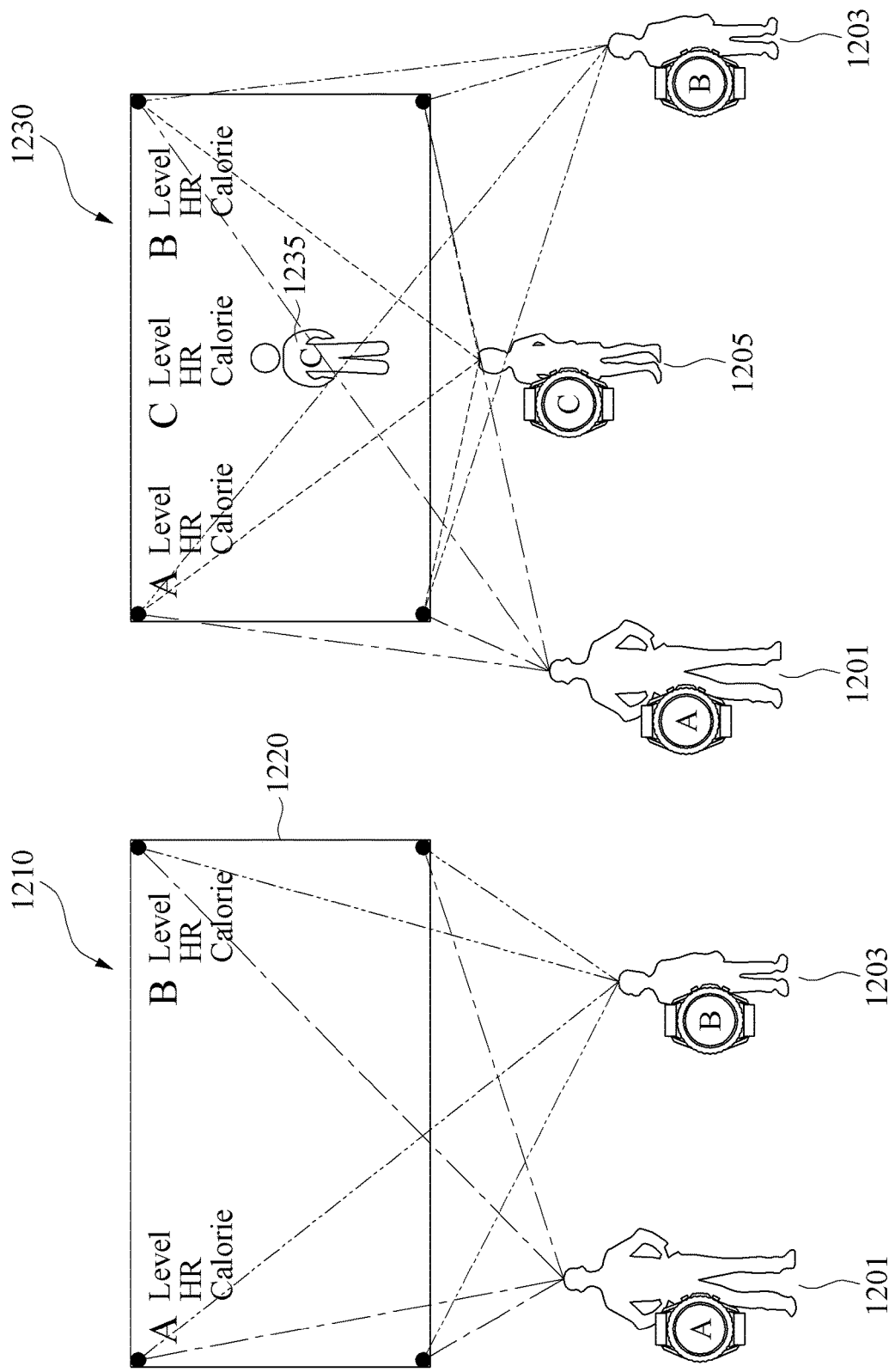
FIG. 12 is a diagram illustrating an operation of an electronic device when another portable device newly enters a recognition space according to one embodiment.
Figure 13:
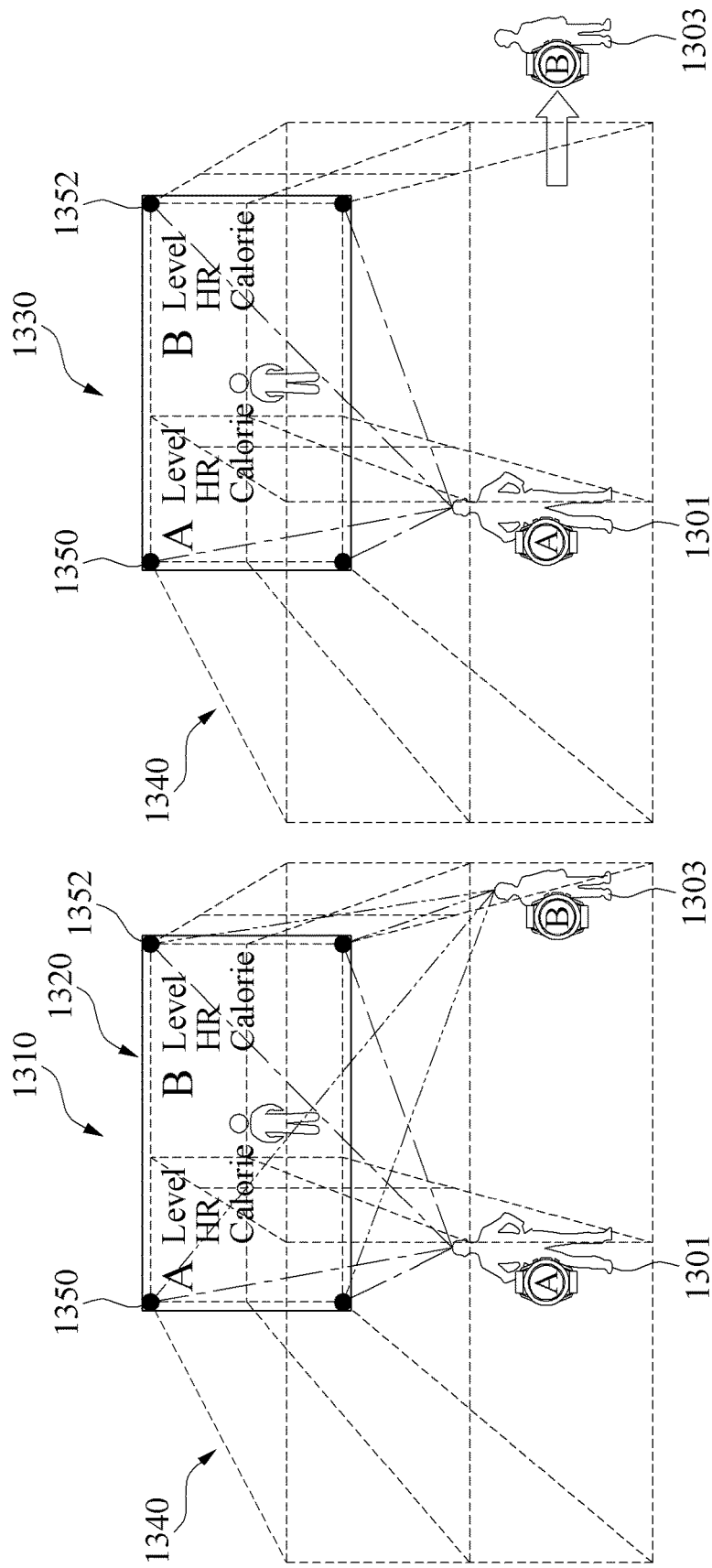
FIG. 13 is a diagram illustrating an operation of an electronic device when a portable device leaves a recognition space according to one embodiment.

The recognition space 630 may refer, for example, to a three-dimensional virtual space in which the electronic device 610 may recognize a user wearing a portable device (e.g., the electronic device 101 of FIG. 1, the portable device 200 of FIGS. 2A and 2B, the wearable device 430 of FIG. 4, the portable device 720 of FIG. 7, the portable device 820 of FIG. 8, the portable device 930 of FIG. 9, the portable device 1003 of FIG. 10, the portable devices 1201, 1203, and 1205 of FIG. 12, the portable devices 1301 and 1303 of FIG. 13, and/or the portable devices 1401, 1403, and 1405 of FIG. 14). The electronic device 610 may define the three-dimensional recognition space 630 having x, y, and z axes based on a space positioned in the front side (e.g., the +z direction of FIG. 6) of the display panel 620 (e.g., the display panel 412 of FIG. 4).

The electronic device 610 may set the virtual recognition space 630, thereby freely setting the activity radius of the users without the constraints of space due to the camera angle.

The electronic device 610 may measure a relative position between the display panel 620 and the wearable device (e.g., wearable device 430) to distinguish the front, rear, left, right, up, and down directions. The recognition space 630 may vary according to the specification of a connectivity (e.g., via the interface 413 of FIG. 4) of the electronic device 610. The electronic device 610 may freely set the range of the recognition space 630 based on the size of a general indoor space.

For example, the recognition space 630 may have a range corresponding to the size of the display panel 620 of the electronic device 610 or the screen of the electronic device 610. Alternatively, since transmission of a general wireless signal may appear in a circular or spherical shape, the recognition space 630 may have a range in the form of a semicircle or an arc in front of the electronic device 610. In addition, the recognition space 630 may be defined by the walls of a room or indoor space in which the electronic device 610 is positioned. However, embodiments are not limited thereto.

For example, when a user executes exercise content through a large-screen display panel 620, the electronic device 610 may set a space to be utilized for an exercise, that is, the recognition space 630, through a calibration function before the exercise according to the exercise content being started. For example, the electronic device 610 may receive, through antennas (e.g., the plurality of antennas 310 of FIG. 3, the antennas 417 of FIG. 4, and/or the plurality of antennas 911, 913, 915, and 917 of FIG. 9), a first signal transmitted through the wearable device 430 at the boundary of the recognition space 630. The electronic device 610 may define the recognition space 630 based on a position determined through the first signal received by each of the antennas 417. In this case, the first signal transmitted from the wearable device 430 for setting the recognition space 630 may be referred to as a "calibration signal". An example method of defining the recognition space 630 by the electronic device 610 will be described further below with reference to, for example, FIG. 7.

FIG. 7 is a diagram illustrating a method of defining a three-dimensional recognition space by an electronic device according to one embodiment. Referring to FIG. 7, according to an embodiment, diagrams 701, 703, 705, and 707 illustrating processes performed as a user 730 wearing the wearable device 720 (e.g., the electronic device 101 of FIG. 1, the portable device 200 of FIGS. 2A and 2B, the wearable device 430 of FIG. 4, the portable device 820 of FIG. 8, the portable device 930 of FIG. 9, the portable device 1003 of FIG. 10, the portable devices 1201, 1203, and 1205 of FIG. 12, the portable devices 1301 and 1303 of FIG. 13, and/or the portable devices 1401, 1403, and 1405 of FIG. 14) starts a space setting mode in the portable device 720 for setting the recognition space 740 (e.g., the recognition space 630 of FIG. 6, the recognition space 830 of FIG. 8, the recognition space 850 of FIG. 8, and/or the recognition space 1340 of FIG. 13) are shown.

According to an embodiment, the electronic device 710 (e.g., the electronic device 102 of FIG. 1, the electronic device 300 of FIG. 3, the electronic device 410 of FIG. 4, the electronic device 510 of FIG. 5, the electronic device 610 of FIG. 6, the electronic device 810 of FIG. 8, the electronic device 910 of FIG. 9, the electronic device 1001 of FIG. 10, the electronic device 1220 of FIG. 12, the electronic device 1320 of FIG. 13, the electronic device 1420 of FIG. 14, and/or the electronic device 1510 of FIG. 15) and the portable device 720 may each provide a space setting mode for space setting.

As shown in the diagram 701, the user 730 wearing the portable device 720 may start the space setting mode for setting the recognition space 740. For example, an area of the recognition space 740 may be set based on a screen displayed by an image sensor. According to an embodiment, the recognition space 740 may correspond to an exercise space for home training. Since a movement of a user is captured through the image sensor (e.g., a camera sensor or a vision sensor), the area recognized by the image sensor may be displayed on the screen of the electronic device 710. According to an embodiment, the range of the recognition space 740 may be artificially adjusted according to the type of the exercise content.

In addition, since a wireless signal for UWB communication has a wide coverage, the user 730 wearing the portable device 720 may be recognized as being in a space in a front side (e.g., the +z direction of FIG. 6) of the electronic device 710 even when far from the electronic device 710. In an embodiment, the user may artificially set the range of the recognition space 740 through the various methods described above, thereby preventing another user from unnecessarily appearing on the screen even if a wireless signal is detected.

According to an embodiment, an image sensor and/or a camera may be attached to the electronic device 710, or an add-on product may be attached thereto for security issues. In this case, the position at which the image sensor or the camera is mounted or the angle of view of the camera may be different, and accordingly, the range of the recognition space 740 may vary. When the position of the image sensor and/or the camera attached to the electronic device 710 or the angle of view of the camera is different, the range of the recognition space 740 may be artificially corrected by a user.

As the space setting mode is selected in the electronic device 710, a guide for the user 730 of the portable device 720 may be provided through a display panel (e.g., the display panel 412 of FIG. 4 and/or the display panel 620 of FIG. 6) of the electronic device 710. The guide may include a text phrase, a voice, and/or an image (or images) guiding the user 730 of the portable device 720 to be positioned in the boundary area of the recognition space 740 in which the exercise content is utilized. However, embodiments are not limited thereto. The guide may include, for example, a guide phrase of "Move to position A and touch [Set] on your Watch" and an image or a voice indicating the position A may be output together.

At the same time of providing the guide to the user 730 through the screen, the electronic device 710 may set the antennas (e.g., the plurality of antennas 310 of FIG. 3, the antennas 417 of FIG. 4, and/or the antennas 911, 913, 915, and 917 of FIG. 9) to enter a signal receiving mode to receive a signal transmitted from the portable device 720.

When the electronic device 710 provides the guide, the user 730 may move to the position A displayed on the screen of the electronic device 710 and select the "Set" button of the portable device 720 and/or, for example, utter "Set" or "Position set", as shown in the diagram 703. In this case, the position A may correspond to a relative position between the electronic device 710 and the portable device 720. The position A may correspond to the boundary area of the recognition space 740. When the set button is selected and/or the voice of the user "Set" or "Position set" is detected, the portable device 720 may transmit a first signal for space setting. The plurality of antennas (e.g., the plurality of antennas 310 of FIG. 3, the antennas 417 of FIG. 4, and/or the plurality of antennas 911, 913, 915, and 917 of FIG. 9) respectively disposed at two or more symmetrical positions among the top, bottom, left, and right of the display panel 620 of the electronic device 710 may receive the first signal transmitted by the portable device 720 in the boundary area at the position A at different (first) times $T_{d1}$, $T_{d2}$, $T_{d3}$, and $T_{d4}$.

When each of the plurality of antennas (e.g., antennas 911, 913, 915, and 917) successfully receives the first signal transmitted from the portable device 720 in the boundary area at the position A according to the guide, the electronic device 710 may provide a guide for next position recognition as shown in the diagram 705. In this case, the guide may be a guide for guiding the user to move to a location B, which is a next boundary area adjacent to the boundary area of the location A. The guide may include, for example, a guide phrase for next position recognition of "Position A recognized. Move to position B and touch [Set] on your Watch" and an image or a voice indicating the position B may be output together.

When the electronic device 710 provides the guide that requests the user to move to the position B, the user 730 may move to the position B displayed on the screen of the electronic device 710 and select the "Set" button of the portable device 720, as shown in the diagram 707. As the Set button is selected, the portable device 720 may transmit a first signal for space setting. One or more of the plurality of antennas (e.g., antennas 911, 913, 915, and 917) respectively disposed at two or more symmetrical positions among the top, bottom, left, and right of the display panel (e.g., display panel 620) of the electronic device 710 may receive the first signal transmitted by the portable device 720 in the boundary area at the position B at different (second) times $T_{d1}$, $T_{d2}$, $T_{d3}$, and $T_{d4}$.

The electronic device 710 may repeat the processes shown in the diagrams 701 through 707, and thereby complete the settings for four boundary areas (e.g., the boundary area at the position A, the boundary area at the position B, a boundary area at a position C, and/or a boundary area at a position D) of each space. For example, the area corresponding to the upper left corner of the display panel 620 of the electronic device 710 may correspond to the position A, and the area corresponding to the upper right corner of the display panel 620 may correspond to the position B. The area corresponding to the lower left corner of the display panel 620 may correspond to the position C, and the area corresponding to the lower right corner of the display panel 620 may correspond to the position D.

When each of the plurality of antennas (e.g., antennas 911, 913, 915, and 917) successfully receives the transmitted first signal in the four boundary areas, the electronic device 710 may define the recognition space 740 using the first signal received by each of the plurality of antennas (e.g., antennas 911, 913, 915, and 917).

FIG. 8 is a diagram illustrating examples of a recognition space defined by an electronic device based on first signals transmitted from portable devices according to one embodiment.

An electronic device 810 may define the recognition space 830 (e.g., the recognition space 630 of FIG. 6, the recognition space 740 of FIG. 7, and/or the recognition space 1340 of FIG. 13) in an area larger than a screen, as shown in a diagram 801. For example, the electronic device 810 may set an area corresponding to 1.5 times the width of the screen of the electronic device 810 as a horizontal boundary area, and define the recognition space 830 by providing a guide to the user wearing the portable device 820 to move to the four boundary areas (e.g., the boundary area at the position A, the boundary area at the position B, the boundary area at the position C, and/or the boundary area at the position D).

As another example, the electronic device 810 may define an area smaller than the screen as the recognition space 850, as shown in the diagram 803. For example, the electronic device 810 may set an area corresponding to 0.8 times the size of the screen of the electronic device 810 as a horizontal and vertical boundary area, and define the recognition space 850 by providing a guide to the user wearing the portable device 820 to move to the four boundary areas (e.g., the boundary area at the position A, the boundary area at the position B, the boundary area at the position C, and/or the boundary area at the position D).

FIG. 9 is a diagram illustrating a method of calculating, by an electronic device, positions of portable devices based on second signals transmitted from the portable devices according to one embodiment. Referring to FIG. 9, the portable device 930 transmitting a second signal to the plurality of antennas 911, 913, 915, and 917 (e.g., the plurality of antennas 310 of FIG. 3 and/or the antennas 417 of FIG. 4) disposed at symmetrical positions of top, bottom, left, and right of a display panel (e.g., the display panel 620 of FIG. 6) of the electronic device 910 is shown.

The electronic device 910 may calculate a first relative position between the portable device 930 positioned in a front side (e.g., the +z direction of FIG. 6) of the display module 350 and the electronic device 910, using differences in the times $T_{d1}$, $T_{d2}$, $T_{d3}$, and $T_{d4}$ at which the antennas 911, 913, 915, and 917 disposed at the symmetrical positions receive the second signal. For example, it may take 4 seconds ($T_{d1}$) for the first antenna to receive the second signal, and it may take 2.5 seconds ($T_{d2}$) for the second antenna to receive the second signal. Further, it may take 3 seconds ($T_{d3}$) for the third antenna to receive the second signal, and it may take 1 second ($T_{d4}$) for the fourth antenna to receive the second signal. These examples times are provided by way of illustration and explanation and do not necessarily reflect the times that would be involved in an actual implementation.

For example, the electronic device 910 may calculate, by the TDoA method, the first relative position between the portable device 930 and the electronic device 910 based on the differences in the times at which the antennas 911, 913, 915, and 917 receive the second signal. The following various methods may be used to calculate the first relative position between the portable device 930 and the electronic device 910.

For example, the electronic device 910 may receive a signal unilaterally transmitted by the portable device 930 (e.g., a signal broadcast through Bluetooth or WiFi), and measure a distance based on a signal strength of the received signal. As such, the method of measuring the distance based on the signal strength of the received signal may be referred to as the received signal strength (RSS) method.

In contrast, UWB communication uses the time of flight (ToF) method or the round trip time (RTT) method and thus, may be performed in a manner that the electronic device 910 transmits a first signal to the portable device 930 and the portable device 930 having received the first signal transmits a second signal back to the electronic device 910. The time-based UWB communication may exhibit relatively high positioning accuracy compared to the RSS method. Further, based on the time difference between the plurality of antennas 911, 913, 915, and 917 of the electronic device 910, it is possible to determine the direction of the portable device 930 relative to the electronic device 910 as well as the distance between the electronic device 910 and the portable device 930.

In addition, a method of measuring the distance between the electronic device 910 and the portable device 930 based on time information when the portable device 930 transmits a wireless signal (e.g., a method that uses the global positioning system (GPS) may be used.

Hereinafter, a method of measuring the distance between the electronic device 910 and the portable device 930 mainly using the ToF method or the RTT method by UWB communication will be described, but the disclosure is not limited in this respect.

As shown in FIG. 9, the electronic device 910 may include a plurality of UWB antennas 911, 913, 915, and 917 arranged in the form of an array.

For example, when the antenna 911 or 915 disposed on the left side of the display panel and the antenna 913 or 917 disposed on the right side of the display panel exchange signals with the portable device 930 by the RTT method, the distance from the left side and the distance from the right side relative to the portable device 930 in the front side (e.g., the +z direction of FIG. 6) of the electronic device 910 may be measured (calculated), respectively, based on the position of the user. In this case, if the distance difference between the left side and the right side is close to "0", the electronic device 910 may determine that the portable device 930 is in the center of the front side (e.g., the +z direction of FIG. 6) of the electronic device 910. Conversely, if the distance from the left side is relatively short compared to the distance from the right side, the electronic device 910 may determine that the portable device 930 is positioned on the left side relative to the center of the electronic device 910.

Likewise, the electronic device 910 may estimate the height of the portable device 930 using the antenna 911 or 913 disposed at the top of the display panel and the antenna 915 or 917 disposed at the bottom of the display panel.

Further, the electronic device 910 may estimate the position of the portable device 930 relative to the electronic device 910 in the recognition space based on the distance obtained through the above process, a horizontal angle obtained using the left-right difference, and a vertical angle obtained using the top-bottom difference. In this case, the estimated distance may have an error within, for example, about 5 cm, and the angle may have an error within, for example, about ±5 degrees. The estimation errors may vary depending on, for example, the number of antennas or the system accuracy, and embodiments are not limited thereto.

The electronic device 910 may calculate the position and/or the height of the portable device 930 by measuring the signal transmission times between the multiple antennas 911, 913, 915, and 917 whose positions are known and the portable device 930, which is a signal source, using the various methods described above.

FIG. 10 is a diagram illustrating transmission and reception sequences between a plurality of antennas of an electronic device and portable devices according to one embodiment. Referring to FIG. 10, according to an embodiment, a diagram 1000 illustrating a situation in which N antennas Antenna 1, Antenna 2, . . . , Antenna N (e.g., the plurality of antennas 310 of FIG. 3, the antennas 417 of FIG. 4, and/or the plurality of antennas 911, 913, 915, and 917 of FIG. 9) disposed in the electronic device 1001 (e.g., the electronic device 102 of FIG. 1, the electronic device 300 of FIG. 3, the electronic device 410 of FIG. 4, the electronic device 510 of FIG. 5, the electronic device 610 of FIG. 6, the electronic device 710 of FIG. 7, the electronic device 810 of FIG. 8, the electronic device 910 of FIG. 9, the electronic device 1220 of FIG. 12, the electronic device 1320 of FIG. 13, the electronic device 1420 of FIG. 14, and/or the electronic device 1510 of FIG. 15) each receive signals transmitted by N portable devices Watch 1, . . . , Watch N (e.g., the electronic device 101 of FIG. 1, the portable device 200 of FIGS. 2A and 2B, the wearable device 430 of FIG. 4, the portable device 720 of FIG. 7, the portable device 820 of FIG. 8, the portable device 930 of FIG. 9, the portable device 1003 of FIG. 10, the portable devices 1201, 1203, and 1205 of FIG. 12, the portable devices 1301 and 1303 of FIG. 13, and/or the portable devices 1401, 1403, and 1405 of FIG. 14) is shown. The N portable devices may be, for example, watch-type portable devices. However, embodiments are not limited thereto.

The distance estimation method performed by the electronic device 1001 using the TDoA of a signal may include at least one of a unidirectional distance estimation method or a bidirectional distance estimation method.

For example, when the unidirectional distance estimation method is used, the electronic device 1001 may estimate the distance based on delay times from the portable device 1003, which is a transmission signal source, to the antennas Antenna 1, Antenna 2, . . . , Antenna N of the electronic device 1001, which are reception signal sources, in a passive situation in which only a second signal is received. The electronic device 1001 may estimate the distance by multiplying a delay time (e.g., a time difference) at which the second signal transmitted from the portable device 1003 is received by the speed, thereby calculating a first relative position, in other words, the distance between the portable device 1003 and an antenna having received the second signal.

For example, when the bidirectional distance estimation method is used, the electronic device 1001 may estimate the distance based on a bidirectional signal that the second signal is transmitted by the portable device 1003 back to the transmission direction in response to the reception of the first signal, in an active situation in which the first signal is transmitted to the portable device 1003. Since the bidirectional signal is used, the electronic device 1001 may estimate the distance by multiplying half the delay time by the speed. The electronic device 1001 may obtain a correlation between a time-delayed waveform of the second signal transmitted from the portable device 1003 and a non-time-delayed waveform of the second signal as a function of the time delay and then, calculate the distance between the portable device 1003 and the antenna having received the second signal by estimating a time delay having the greatest correlation value as the TDoA.

The portable device 1003 may transmit signals to the electronic device 1001 by dividing time and receive signals sequentially transmitted from the electronic device 1001, thereby measuring the distances between the portable device 1003 and the antennas having received the signals and/or the directions of the antennas.

The electronic device 1001 may operate based on, for example, the TDoA method. When the signals transmitted from the portable devices 1003 are received by the antennas (e.g., the antennas 911, 913, 915, and 917 of FIG. 9) embedded in the front side (e.g., the +z direction of FIG. 6) of the display module (e.g., the display module 350 of FIG. 3) of the electronic device 1001, a RTLS (e.g., the RTLS 416 of FIG. 4) of the electronic device 1001 may obtain device information (e.g., device types and/or device identification (ID) information) and $T_{dx}$ (e.g., $T_{d1}$, $T_{d2}$, $T_{d3}$, and $T_{d4}$) information of the portable devices 1003 from the signals received by the respective antennas 911, 913, 915, and 917. The electronic device 1001 may identify the portable devices 1003 based on the device information of the portable devices 1003, and calculate relative positions between the front side (e.g., the +z direction of FIG. 6) of the display module (e.g., the display module 350 of FIG. 3) and the portable devices 1003 based on the $T_{dx}$ information. A time slot may be construed as a time used for each of the antennas 911, 913, 915, and 917 of the electronic device 1001 to receive all signals transmitted by any one portable device. For example, the portable devices may sequentially transmit signals to the electronic device 1001 for each time slot. However, embodiments are not limited thereto.

The number of antennas 911, 913, 915, and 917 disposed in the electronic device 1001 may be increased, and the number of portable devices 1003 may also be increased. According to an embodiment, the minimum number of antennas disposed in the electronic device 1001 may be reduced. For example, two or three antennas may be disposed symmetrically on the left and the right.

Figure 11:
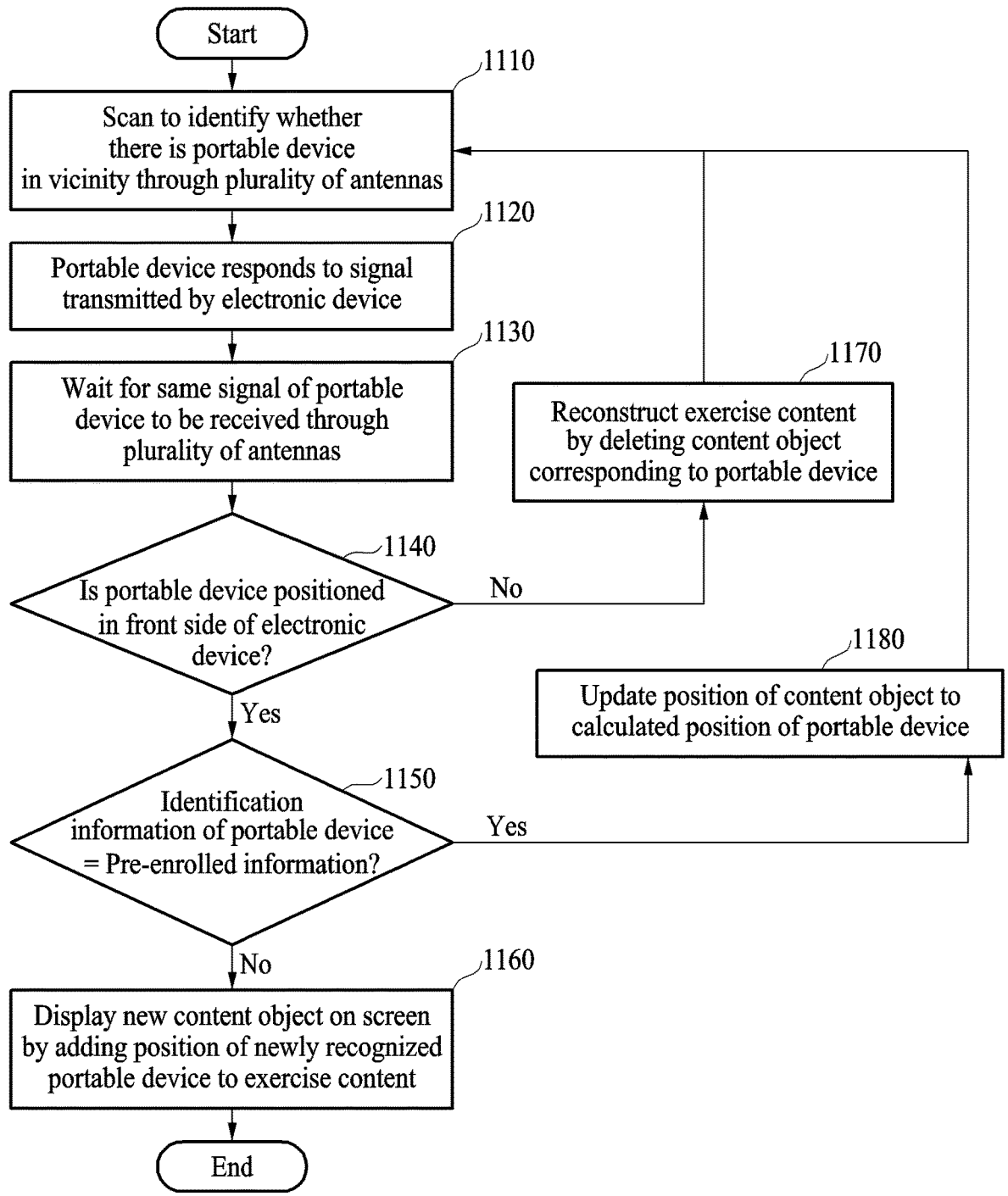
FIG. 11 is a flowchart illustrating a method of updating an exercise content by an electronic device according to one embodiment.

FIG. 11 is a flowchart illustrating a method of updating an exercise content by an electronic device according to one embodiment. In the following example embodiments, operations may be performed sequentially, but are not necessarily performed sequentially. For example, the operations may be performed in different orders, and/or at least two of the operations may be performed in parallel.

Referring to FIG. 11, according to an embodiment, an electronic device (e.g., the first electronic device 102 of FIG. 1, the electronic device 300 of FIG. 3, the electronic device 410 of FIG. 4, the electronic device 510 of FIG. 5, the electronic device 610 of FIG. 6, the electronic device 710 of FIG. 7, the electronic device 810 of FIG. 8, the electronic device 910 of FIG. 9, the electronic device 1001 of FIG. 10, the electronic device 1220 of FIG. 12, the electronic device 1320 of FIG. 13, the electronic device 1420 of FIG. 14, and/or the electronic device 1510 of FIG. 15) may provide exercise content through operations 1110 to 1180.

In operation 1110, the electronic device 1001 (e.g., the processor 330 of FIG. 3 or the processor 414 of FIG. 4) may scan to identify whether there is a portable device (e.g., the electronic device 101 of FIG. 1, the portable device 200 of FIGS. 2A and 2B, the wearable device 430 of FIG. 4, the portable device 720 of FIG. 7, the portable device 820 of FIG. 8, the portable device 930 of FIG. 9, the portable device 1003 of FIG. 10, the portable devices 1201, 1203, and 1205 of FIG. 12, the portable devices 1301 and 1303 of FIG. 13, and/or the portable devices 1401, 1403, and 1405 of FIG. 14) in the vicinity thereof, through a plurality of antennas (e.g., the plurality of antennas 310 of FIG. 3, the antennas 417 of FIG. 4, and/or the plurality of antennas 911, 913, 915, and 917 of FIG. 9).

When a portable device 1003 identified by the scanning in operation 1110 responds to a signal transmitted by the electronic device 1001 (e.g., the processor 330 of FIG. 3 or the processor 414 of FIG. 4) in operation 1120, the electronic device 1001 (e.g., the processor 330 of FIG. 3 or the processor 414 of FIG. 4) may wait for the same signal of the portable device 1003 to be received through the plurality of antennas 911, 913, 915, and 917 in operation 1130.

In operation 1140, the electronic device 1001 (e.g., the processor 330 of FIG. 3 or the processor 414 of FIG. 4) may determine whether the portable device 1003 is positioned in a front side (e.g., the +z direction of FIG. 6) of a display module (e.g., the display module 350 of FIG. 3) of the electronic device 1001. The electronic device 1001 (e.g., the processor 330 of FIG. 3 or the processor 414 of FIG. 4) may determine whether the portable device 1003 is positioned in the front side (e.g., the +z direction of FIG. 6) of the display module of the electronic device 1001 (e.g., the processor 330 of FIG. 3 or the processor 414 of FIG. 4) by analyzing the angle and/or the distance at which the signal transmitted by the portable device 1003 is received. In this case, the electronic device 1001 (e.g., the processor 330 of FIG. 3 or the processor 414 of FIG. 4) may determine whether the portable device 1003 is positioned in a recognition space (e.g., the recognition space 630 of FIG. 6, the recognition space 740 of FIG. 7, the recognition space 830 of FIG. 8, the recognition space 850 of FIG. 8, and/or the recognition space 1340 of FIG. 13) in the front side (e.g., the +z direction of FIG. 6) of the display module 350.

When it is determined in operation 1140 that the portable device 1003 is not positioned in the front side (e.g., the +z direction of FIG. 6) of the electronic device 1001 (e.g., the processor 330 of FIG. 3 or the processor 414 of FIG. 4), the electronic device 1001 (e.g., the processor 330 of FIG. 3 or the processor 414 of FIG. 4) may provide (or reconstruct) exercise content by deleting a content object (e.g., a character, an avatar, an emoji, and/or an emoticon) corresponding to the portable device 1003 from exercise content displayed on the screen in operation 1170, and then perform operation 1110.

Conversely, when it is determined in operation 1140 that the portable device 1003 is positioned in the front side (e.g., the +z direction of FIG. 6) of the electronic device 1001, the electronic device 1001 (e.g., the processor 330 of FIG. 3 or the processor 414 of FIG. 4) may determine whether identification information of the portable device 1003 is pre-enrolled information or newly recognized information, in operation 1150.

When it is determined in operation 1150 that the identification information of the portable device 1003 is pre-enrolled information, the electronic device 1001 (e.g., the processor 330 of FIG. 3 or the processor 414 of FIG. 4) may update the position of the content object corresponding to the portable device 1003 to the calculated position of the portable device 1003 in operation 1180 and then, perform operation 1110.

When it is determined in operation 1150 that the identification information of the portable device 1003 is not pre-enrolled information, the electronic device 1001 (e.g., the processor 330 of FIG. 3 or the processor 414 of FIG. 4) may display a new content object on the screen by adding the position of the newly recognized portable device 1003 to the exercise content, in operation 1160.

FIG. 12 is a diagram illustrating an operation of an electronic device when a portable device newly enters a recognition space according to one embodiment. Referring to FIG. 12, according to an embodiment, a diagram 1210 illustrating a situation in which two users, a user A wearing the portable device 1201 (e.g., the electronic device 101 of FIG. 1, the portable device 200 of FIGS. 2A and 2B, the wearable device 430 of FIG. 4, the portable device 720 of FIG. 7, the portable device 820 of FIG. 8, the portable device 930 of FIG. 9, the portable device 1003 of FIG. 10, the portable devices 1301 and 1303 of FIG. 13, and/or the portable devices 1401, 1403, and 1405 of FIG. 14) and a user B wearing the portable device 1203, are positioned in a recognition space (e.g., the recognition space 630 of FIG. 6, the recognition space 740 of FIG. 7, the recognition space 830 of FIG. 8, the recognition space 850 of FIG. 8, and/or the recognition space 1340 of FIG. 13) of the electronic device 1220 (e.g., the electronic device 102 of FIG. 1, the electronic device 300 of FIG. 3, the electronic device 410 of FIG. 4, the electronic device 510 of FIG. 5, the electronic device 610 of FIG. 6, the electronic device 710 of FIG. 7, the electronic device 810 of FIG. 8, the electronic device 910 of FIG. 9, the electronic device 1001 of FIG. 10, the electronic device 1320 of FIG. 13, the electronic device 1420 of FIG. 14, and/or the electronic device 1510 of FIG. 15), and a diagram 1230 illustrating a situation in which a user C wearing the portable device 1205 newly enters the same recognition space are shown.

The electronic device 1220 may exchange signals (e.g., a first signal and/or a second signal) with the plurality of portable devices 1201, 1203, and 1205 positioned on the front side (e.g., the +z direction of FIG. 6) of the electronic device 1220 in real time through multiple antennas (e.g., the plurality of antennas 310 of FIG. 3, the antennas 417 of FIG. 4, and/or the plurality of antennas 911, 913, 915, and 917 of FIG. 9). In this case, signals transmitted by the portable devices 1201, 1203, and 1205 may be received by the antennas 911, 913, 915, and 917 embedded in the front side (e.g., the +z direction of FIG. 6) of a display module (e.g., the display module 350 of FIG. 3) of the electronic device 1220. A RTLS (e.g., the RTLS 416 of FIG. 4) of the electronic device 1220 may identify the portable devices 1201, 1203, and 1205 by receiving device information of each of the portable devices 1201, 1203, and 1205, and may calculate first relative positions between the front side (e.g., the +z direction of FIG. 6) of the display module 350 and the portable devices 1201, 1203, and 1205 based on Tax information received by each of the antennas 911, 913, 915, and 917.

The electronic device 1220 may identify whether each of the portable devices 1201, 1203, and 1205 is positioned in the recognition space 1340 based on the first relative positions. The electronic device 1220 may also calculate a second relative position between the portable devices 1201, 1203, and 1205, and display a user content object (e.g., a character, an avatar, an emoji, and/or an emoticon) corresponding to each of the portable devices 1201, 1203, and 1205 at a corresponding position in exercise content displayed on the screen. In this case, the electronic device 1220 may detect the positions of all portable devices 1201, 1203, and 1205 detectable on the front side (e.g., the +z direction of FIG. 6), even without the initial settings for recognizing the portable devices 1201, 1203, and 1205.

After the positions of the users are determined in the exercise content according to the relative positions of the portable devices 1201 and 1203 recognized in the front side (e.g., the +z direction of FIG. 6) of the electronic device 1220 as shown in the diagram 1210, a new user C wearing the portable device 1205 may be additionally recognized as shown in the diagram 1230. In this case, the electronic device 1220 may automatically adjust the positions of the user content objects disposed on the screen by calculating the relative position (e.g., the second relative position) between the portable devices 1201, 1203, and 1205 that the users A, B, and C are wearing, irrespective of the order in which the portable devices 1201, 1203, and 1205 that the users are wearing are recognized.

When it is identified that the portable device 1205 that the user C is wearing is positioned in the 3D recognition space as shown in the diagram 1230, the electronic device 1220 may determine whether identification information of the portable device 1205 that the user C is wearing is pre-enrolled information. The electronic device 1220 may provide or reconstruct the exercise content with a character 1235 corresponding to the portable device 1205 according to whether the identification information of the portable device 1205 is pre-enrolled information.

For example, when it is determined that the identification information of the portable device 1205 is pre-enrolled information, the electronic device 1220 may update the position of the character 1235 corresponding to the portable device 1205 displayed in the exercise content, based on the first relative position between the electronic device 1220 and the portable device 1205.

Conversely, when it is determined that the identification information of the portable device 1205 is not pre-enrolled information, the electronic device 1220 may add a new character 1235 corresponding to the portable device 1205 that newly enters the recognition space 1340 to the exercise content. In this case, the new character 1235 may be displayed in the exercise content by reflecting the position of the portable device 1205 that newly enters the recognition space 1340.

FIG. 13 is a diagram illustrating an operation of an electronic device when a portable device leaves a recognition space according to one embodiment. Referring to FIG. 13, according to an embodiment, a diagram 1310 illustrating a situation in which two users, a user A wearing the portable device 1301 and a user B wearing the portable device 1303 (e.g., the electronic device 101 of FIG. 1, the portable device 200 of FIGS. 2A and 2B, the wearable device 430 of FIG. 4, the portable device 720 of FIG. 7, the portable device 820 of FIG. 8, the portable device 930 of FIG. 9, the portable device 1003 of FIG. 10, the portable devices 1201, 1203, and 1205 of FIG. 12, and/or the portable devices 1401, 1403, and 1405 of FIG. 14), are positioned in the recognition space 1340 (e.g., the recognition space 630 of FIG. 6, the recognition space 740 of FIG. 7, the recognition space 830 of FIG. 8, and/or the recognition space 850 of FIG. 8) of the electronic device 1320 (e.g., the electronic device 102 of FIG. 1, the electronic device 300 of FIG. 3, the electronic device 410 of FIG. 4, the electronic device 510 of FIG. 5, the electronic device 610 of FIG. 6, the electronic device 710 of FIG. 7, the electronic device 810 of FIG. 8, the electronic device 910 of FIG. 9, the electronic device 1001 of FIG. 10, the electronic device 1220 of FIG. 12, the electronic device 1420 of FIG. 14, and/or the electronic device 1510 of FIG. 15), and a diagram 1330 illustrating a situation in which the user B wearing the portable device 1303 leaves the recognition space 1340 are shown.

While the users A and B are using exercise content provided by the electronic device 1320 as shown in the diagram 1310, the user B may leave the recognition space 1340 (e.g., the recognition space 630 of FIG. 6, the recognition space 740 of FIG. 7, and/or the recognition space 830 of FIG. 8, and the recognition space 850 of FIG. 8) that is previously defined, as shown in the diagram 1330. In this case, whether the user B leaves the previously defined recognition space 1340 may be estimated or determined by the following methods.

For example, when the user B included in a field of view (FOV) of the antenna A 1350 of the electronic device 1320 and in a FOV of the antenna B 1352 of the electronic device 1320 in the recognition space 1340 leaves the recognition space 1340, the portable device 1203 that the user B is wearing may not be detected in the FOV of the antenna B 1352. Accordingly, the electronic device 1320 may estimate or determine that the user B leaves the recognition space 1340. Alternatively, when a time at which a signal transmitted by the portable device 1303 that the user B is wearing is received is beyond a threshold for the difference of (transmission time-reception time), the electronic device 1320 may estimate or determine that the user B leaves the recognition space 1340.

As described above, the electronic device 1320 may identify whether the portable devices 1301 and 1303 leave the recognition space 1340 or newly enter the recognition space 1340, based on signals (e.g., second signals) transmitted by the portable devices 1301 and 1303, while a display module (e.g., the display module 350 of FIG. 3) is displaying the exercise content.

When it is estimated that the portable device 1303 that the user B is wearing is not positioned in the recognition space 1340, that is, it is estimated that the portable device 1303 leaves the recognition space 1340, a RTLS (e.g., the RTLS 416 of FIG. 4) of the electronic device 1320 receiving the signal of the portable device 1303 that the user B is wearing may reconstruct or provide the exercise content by deleting a content object (e.g., a character, an avatar, an emoji, and/or an emoticon) corresponding to the leaving portable device 1303 from the exercise content. The RTLS 416 of the electronic device 1320 may remove, from the screen, information about the user B including the content object corresponding to the user B in the exercise content. In this case, the information about the user B may include, for example, the exercise level of the user B, the heart rate of the user B, the consumed calories of the user B according to an exercise, and the body temperature of the user B. However, embodiments are not limited thereto.

FIG. 14 is a diagram illustrating a method of reconstructing an exercise content in response to changes in the positions of portable devices positioned in a recognition space according to one embodiment. Referring to FIG. 14, according to an embodiment, a diagram 1410 illustrating a situation in which a user A wearing the portable device 1401 (e.g., the electronic device 101 of FIG. 1, the portable device 200 of FIGS. 2A and 2B, the wearable device 430 of FIG. 4, the portable device 720 of FIG. 7, the portable device 820 of FIG. 8, the portable device 930 of FIG. 9, the portable device 1003 of FIG. 10, the portable devices 1201, 1203, and 1205 of FIG. 12, and/or the portable devices 1301 and 1303 of FIG. 13), a user B wearing the portable device 1403, and a user C wearing the portable device 1405 are positioned in a recognition space (e.g., the recognition space 630 of FIG. 6, the recognition space 740 of FIG. 7, the recognition space 830 of FIG. 8, the recognition space 850 of FIG. 8, and/or the recognition space 1340 of FIG. 13) on a front side (e.g., the +z direction of FIG. 6) of the electronic device 1420 (e.g., the electronic device 102 of FIG. 1, the electronic device 300 of FIG. 3, the electronic device 410 of FIG. 4, the electronic device 510 of FIG. 5, the electronic device 610 of FIG. 6, the electronic device 710 of FIG. 7, the electronic device 810 of FIG. 8, the electronic device 910 of FIG. 9, the electronic device 1001 of FIG. 10, the electronic device 1220 of FIG. 12, the electronic device 1320 of FIG. 13, and/or the electronic device 1510 of FIG. 15), and diagrams 1430 and 1450 illustrating situations in which the positions of the users change are shown.

For example, when a plurality of portable devices 1401, 1403, and 1405 are positioned in the recognition space, the electronic device 1420 may calculate second relative positions between the plurality of portable devices 1401, 1403, and 1405 based on first relative positions between the electronic device 1420 and the plurality of portable devices 1401, 1403, and 1405.

The electronic device 1420 may identify whether there are a plurality of portable devices 1401, 1403, and 1405, based on second signals transmitted by the plurality of portable devices 1401, 1403, and 1405. When it is identified that the plurality of portable devices 1401, 1403, and 1405 move to new positions, the electronic device 1420 may track the new positions of the plurality of portable devices 1401, 1403, and 1405. The electronic device 1420 may reconstruct or provide exercise content by adjusting at least one of the positions, exercise information, or sizes of content objects (e.g., characters, avatars, emojis, and or emoticons) corresponding to the plurality of portable devices 1401, 1403, and 1405 based on the tracked positions.

The electronic device 1420 may provide exercise content for an exercise that a plurality of users may participate in, such as dancing. In this case, the electronic device 1420 may construct or provide exercise content by reflecting a group choreography among the plurality of users and position change information of the users. The electronic device 1420 may track changes in the positions of the user A, the user B, and the user C who are provided with the exercise content, and display exercise information corresponding to each user on the screen by reflecting the tracked position changes of the users.

For example, when the users arranged as shown in the diagram 1410 move to new positions as shown in the diagram 1430 or 1450, the electronic device 1420 may detect the movements of the portable devices to the front, rear, left, and right based on signals transmitted by the portable device 1401 that the user A is wearing, the portable device 1403 that the user B is wearing, and the portable device 1405 that the user C is wearing. For example, when the user C positioned at the front and center of the electronic device 1420 in the diagram 1410 moves to the left as shown in the diagram 1430, the electronic device 1420 may detect the movement of the user C based on the signal transmitted by the portable device 1405 that the user C is wearing. In this case, the electronic device 1420 may reconstruct or provide the exercise content such that the exercise information corresponding to the user C and/or the content object corresponding to the user C displayed on the screen is moved and displayed to the left side in proportion to the distance the user C moves, as shown in the diagram 1430. In addition, the user A positioned behind the user C on the front side (e.g., the +z direction of FIG. 6) of the electronic device 1420 may move to the center position on the front side (e.g., the +z direction of FIG. 6) of the electronic device 1420, as shown in the diagram 1450. In this case, the electronic device 1420 may track the user A who moves to the center based on the signal transmitted by the portable device 1401 that the user A is wearing. The electronic device 1420 may display the content object corresponding to the user A and/or the exercise information of the user A at the center position on the screen on which the exercise content is displayed, by reflecting the new position of the user A.

When the exercise content provided by the electronic device 1420 is a dance content, the arrangement and/or positions of the users may change according to motions provided by the dance content, and motions of the users may change. For example, according to the exercise content provided by the electronic device 1420, the user A may perform a sitting motion, and the user B and the user C may perform jumping motions. In this case, the electronic device 1420 may reconstruct or provide the exercise content by adjusting the poses, positions, and sizes of the characters corresponding to the users by reflecting the different motions of the users.

As described above, the electronic device 1420 may adjust the characters, the exercise information, and the sizes of the characters displayed on the screen by reflecting the movements of the users, thereby allowing the users to three-dimensionally experience the movements in the recognition space. Further, the electronic device 1420 may reconstruct the exercise content to interact with the physical actions of the users based on the relative position between the users, thereby improving the immersion of the users.

FIG. 15 is a diagram illustrating an example of displaying the positions of a plurality of users in exercise content when the plurality of users perform a group exercise wearing portable devices according to one embodiment. Referring to FIG. 15, a diagram 1500 illustrating a situation in which a plurality of users perform a group exercise at fixed positions according to an instruction of an instructor is shown.

The electronic device 1510 (e.g., the electronic device 102 of FIG. 1, the electronic device 300 of FIG. 3, the electronic device 410 of FIG. 4, the electronic device 510 of FIG. 5, the electronic device 610 of FIG. 6, the electronic device 710 of FIG. 7, the electronic device 810 of FIG. 8, the electronic device 910 of FIG. 9, the electronic device 1001 of FIG. 10, the electronic device 1220 of FIG. 12, the electronic device 1320 of FIG. 13, and/or the electronic device 1420 of FIG. 14) may display exercise information (e.g., the consumed calories, the exercise durations, the body temperatures, and/or the heart rates) corresponding to a plurality of users wearing portable devices (e.g., the electronic device 101 of FIG. 1, the portable device 200 of FIGS. 2A and 2B, the wearable device 430 of FIG. 4, the portable device 720 of FIG. 7, the portable device 820 of FIG. 8, the portable device 930 of FIG. 9, the portable device 1003 of FIG. 10, the portable devices 1201, 1203, and 1205 of FIG. 12, and/or the portable devices 1301 and 1303 of FIG. 13) on the screen.

FIG. 16 is a flowchart illustrating an operating method of an electronic device according to one embodiment. In the following embodiments, operations may be performed sequentially, but are not necessarily performed sequentially. For example, the operations may be performed in different orders, and/or at least two of the operations may be performed in parallel.

Referring to FIG. 16, according to an embodiment, an electronic device (e.g., the electronic device 102 of FIG. 1, the electronic device 300 of FIG. 3, the electronic device 410 of FIG. 4, the electronic device 510 of FIG. 5, the electronic device 610 of FIG. 6, the electronic device 710 of FIG. 7, the electronic device 810 of FIG. 8, the electronic device 910 of FIG. 9, the electronic device 1001 of FIG. 10, the electronic device 1220 of FIG. 12, the electronic device 1320 of FIG. 13, the electronic device 1420 of FIG. 14, and/or the electronic device 1510 of FIG. 15) may display exercise content through operations 1610 to 1650.

In operation 1610, the electronic device (e.g., the processor 330 of FIG. 3 or the processor 414 of FIG. 4) may scan to identify whether there is at least one portable device (e.g., the electronic device 101 of FIG. 1, the portable device 200 of FIGS. 2A and 2B, the wearable device 430 of FIG. 4, the portable device 720 of FIG. 7, the portable device 820 of FIG. 8, the portable device 930 of FIG. 9, the portable device 1003 of FIG. 10, the portable devices 1201, 1203, and 1205 of FIG. 12, the portable devices 1301 and 1303 of FIG. 13, and/or the portable devices 1401, 1403, and 1405 of FIG. 14), using a plurality of antennas (e.g., the plurality of antennas 310 of FIG. 3, the antennas 417 of FIG. 4, and/or the plurality of antennas 911, 913, 915, and 917 of FIG. 9) for wireless communication.

In operation 1620, the electronic device (e.g., the processor 330 of FIG. 3 or the processor 414 of FIG. 4) may define a three-dimensional recognition space (e.g., the recognition space 630 of FIG. 6, the recognition space 740 of FIG. 7, the recognition space 830 of FIG. 8, the recognition space 850 of FIG. 8, and/or the recognition space 1340 of FIG. 13) based on a first signal transmitted from the wearable device 430, scanned in operation 1610, for space setting. For example, in response to a space setting mode being started in the wearable device 430 for setting the recognition space 630, the electronic device (e.g., the processor 330 of FIG. 3 or the processor 414 of FIG. 4) may provide a guide for a user of the wearable device 430. In this case, the guide may include, for example, a voice and/or an image guiding the wearable device 430 to be positioned in a boundary area of the recognition space 630 in which the exercise content is utilized. However, embodiments are not limited thereto. The electronic device (e.g., the processor 330 of FIG. 3 or the processor 414 of FIG. 4) may receive the first signal transmitted from the wearable device 430 in the boundary area according to the guide. When each of the plurality of antennas (e.g., antennas 911, 913, 915, and 917) successfully receives the first signal, the electronic device (e.g., the processor 330 of FIG. 3 or the processor 414 of FIG. 4) may define the recognition space 630 using the first signal received by each of the plurality of antennas (e.g., antennas 911, 913, 915, and 917).

In operation 1630, the electronic device (e.g., the processor 330 of FIG. 3 or the processor 414 of FIG. 4) may calculate the position of the wearable device 430 in the recognition space 630, defined in operation 1620, based on a second signal transmitted from the wearable device 430. The electronic device (e.g., the processor 330 of FIG. 3 or the processor 414 of FIG. 4) may identify whether the wearable device 430 includes a plurality of wearable devices 430, based on the second signal. When it is identified that the plurality of wearable devices 430 move to new positions, the electronic device (e.g., the processor 330 of FIG. 3 or the processor 414 of FIG. 4) may track the new positions of the plurality of wearable devices 430.

In operation 1640, the electronic device (e.g., the processor 330 of FIG. 3 or the processor 414 of FIG. 4) may generate exercise content based on the position(s) of the wearable device 430 identified in operation 1630. The electronic device (e.g., the processor 330 of FIG. 3 or the processor 414 of FIG. 4) may reconstruct or provide the exercise content by adjusting at least one of the positions, exercise information, or sizes of content objects (e.g., characters, avatars, emojis, and or emoticons) corresponding to the plurality of wearable devices 430 based on the positions identified or tracked in operation 1630.

In operation 1650, the electronic device (e.g., the processor 330 of FIG. 3 or the processor 414 of FIG. 4) may display the exercise content.

According to an embodiment, an electronic device 102, 300, 410, 510, 610, 710, 810, 910, 1001, 1220, 1320, 1420, 1510 may include a plurality of antennas 310, 417, 911, 913, 915, 917 for wireless communication, a processor 330, 414 configured to scan to identify whether there is at least one portable device 101, 200, 430, 720, 820, 930, 1003, 1201, 1203, 1205, 1301, 1303, 1401, 1403, 1405 using the plurality of antennas 310, 417, 911, 913, 915, 917, define a three-dimensional recognition space 630, 740, 830, 850, 1340 based on a first signal transmitted from the portable device 101, 200, 430, 720, 820, 930, 1003, 1201, 1203, 1205, 1301, 1303, 1401, 1403, 1405 for space setting, calculate a position of the portable device 101, 200, 430, 720, 820, 930, 1003, 1201, 1203, 1205, 1301, 1303, 1401, 1403, 1405 in the recognition space 630, 740, 830, 850, 1340 based on a second signal transmitted from the portable device 101, 200, 430, 720, 820, 930, 1003, 1201, 1203, 1205, 1301, 1303, 1401, 1403, 1405, and generate exercise content based on the position of the portable device 101, 200, 430, 720, 820, 930, 1003, 1201, 1203, 1205, 1301, 1303, 1401, 1403, 1405, and a display module 350 configured to display the exercise content.

According to an embodiment, the processor 330, 414 may be configured to define the recognition space 630, 740, 830, 850, 1340 relative to a front side of the display module 350 based on the first signal.

According to an embodiment, the processor 330, 414 may be configured to calculate a first relative position including a distance and an angle between the electronic device 102, 300, 410, 510, 610, 710, 810, 910, 1001, 1220, 1320, 1420, 1510 and the portable device 101, 200, 430, 720, 820, 930, 1003, 1201, 1203, 1205, 1301, 1303, 1401, 1403, 1405 in the recognition space 630, 740, 830, 850, 1340 using a difference in times at which the plurality of antennas 310, 417, 911, 913, 915, 917 receive the second signal.

According to an embodiment, the processor 330, 414 may be configured to provide a user of the portable device 101, 200, 430, 720, 820, 930, 1003, 1201, 1203, 1205, 1301, 1303, 1401, 1403, 1405 with a guide to guide the portable device 101, 200, 430, 720, 820, 930, 1003, 1201, 1203, 1205, 1301, 1303, 1401, 1403, 1405 to be positioned in a boundary area of the recognition space 630, 740, 830, 850, 1340 in which the exercise content is to be utilized, in response to a space setting mode being started in the portable device 101, 200, 430, 720, 820, 930, 1003, 1201, 1203, 1205, 1301, 1303, 1401, 1403, 1405 for setting the recognition space 630, 740, 830, 850, 1340, and set the plurality of antennas 310, 417, 911, 913, 915, 917 to receive the first signal transmitted from the portable device 101, 200, 430, 720, 820, 930, 1003, 1201, 1203, 1205, 1301, 1303, 1401, 1403, 1405 according to the guide.

According to an embodiment, the processor 330, 414 may be configured to provide a guide to guide the portable device 101, 200, 430, 720, 820, 930, 1003, 1201, 1203, 1205, 1301, 1303, 1401, 1403, 1405 to move to a boundary area next to the boundary area, when each of the plurality of antennas 310, 417, 911, 913, 915, 917 successfully receives the first signal transmitted from the portable device 101, 200, 430, 720, 820, 930, 1003, 1201, 1203, 1205, 1301, 1303, 1401, 1403, 1405 in the boundary area according to the guide.

According to an embodiment, the processor 330, 414 may be configured to define the recognition space 630, 740, 830, 850, 1340 using the first signal received by each of the plurality of antennas 310, 417, 911, 913, 915, 917, when each of the plurality of antennas 310, 417, 911, 913, 915, 917 successfully receives the first signal.

According to an embodiment, one or more of the plurality of antennas 310, 417, 911, 913, 915, 917 may be disposed at each of two or more symmetrical positions among top, bottom, left, and right of the display module 350, and the processor 330, 414 may be configured to calculate a first relative position between the electronic device 102, 300, 410, 510, 610, 710, 810, 910, 1001, 1220, 1320, 1420, 1510 and the portable device 101, 200, 430, 720, 820, 930, 1003, 1201, 1203, 1205, 1301, 1303, 1401, 1403, 1405 using a difference in times at which the plurality of antennas 310, 417, 911, 913, 915, 917 disposed at the symmetrical positions receive the second signal.

According to an embodiment, the processor 330, 414 may be configured to identify whether the portable device 101, 200, 430, 720, 820, 930, 1003, 1201, 1203, 1205, 1301, 1303, 1401, 1403, 1405 is positioned in the recognition space 630, 740, 830, 850, 1340 based on the first relative position.

According to an embodiment, the processor 330, 414 may be configured to, when it is identified that the portable device 101, 200, 430, 720, 820, 930, 1003, 1201, 1203, 1205, 1301, 1303, 1401, 1403, 1405 is not positioned in the recognition space 630, 740, 830, 850, 1340, reconstruct the exercise content by deleting a content object corresponding to the portable device 101, 200, 430, 720, 820, 930, 1003, 1201, 1203, 1205, 1301, 1303, 1401, 1403, 1405 from the exercise content.

According to an embodiment, the processor 330, 414 may be configured to, when it is identified that the portable device 101, 200, 430, 720, 820, 930, 1003, 1201, 1203, 1205, 1301, 1303, 1401, 1403, 1405 is positioned in the three-dimensional recognition space 630, 740, 830, 850, 1340, determine whether identification information of the portable device 101, 200, 430, 720, 820, 930, 1003, 1201, 1203, 1205, 1301, 1303, 1401, 1403, 1405 is pre-enrolled information, and reconstruct the exercise content with a content object corresponding to the portable device 101, 200, 430, 720, 820, 930, 1003, 1201, 1203, 1205, 1301, 1303, 1401, 1403, 1405 according to whether the identification information is pre-enrolled information.

According to an embodiment, the processor 330, 414 may be configured to, when it is determined that the identification information of the portable device 101, 200, 430, 720, 820, 930, 1003, 1201, 1203, 1205, 1301, 1303, 1401, 1403, 1405 is pre-enrolled information, update a position of the content object corresponding to the portable device 101, 200, 430, 720, 820, 930, 1003, 1201, 1203, 1205, 1301, 1303, 1401, 1403, 1405 displayed in the exercise content, based on the first relative position.

According to an embodiment, the processor 330, 414 may be configured to, when it is determined that the identification information of the portable device 101, 200, 430, 720, 820, 930, 1003, 1201, 1203, 1205, 1301, 1303, 1401, 1403, 1405 is not pre-enrolled information, add a content object corresponding to the position of the portable device 101, 200, 430, 720, 820, 930, 1003, 1201, 1203, 1205, 1301, 1303, 1401, 1403, 1405 to the exercise content.

According to an embodiment, the processors 330 and 414 may be configured to, when the portable device 101, 200, 430, 720, 820, 930, 1003, 1201, 1203, 1205, 1301, 1303, 1401, 1403, 1405 is a plurality of portable devices 101, 200, 430, 720, 820, 930, 1003, 1201, 1203, 1205, 1301, 1303, 1401, 1403, 1405, calculate second relative positions between the plurality of portable devices 101, 200, 430, 720, 820, 930, 1003, 1201, 1203, 1205, 1301, 1303, 1401, 1403, 1405 based on first relative positions between the electronic device 102, 300, 410, 510, 610, 710, 810, 910, 1001, 1220, 1320, 1420, 1510 and the plurality of portable devices 101, 200, 430, 720, 820, 930, 1003, 1201, 1203, 1205, 1301, 1303, 1401, 1403, 1405.

According to an embodiment, the processor 330, 414 may be configured to identify whether the portable device 101, 200, 430, 720, 820, 930, 1003, 1201, 1203, 1205, 1301, 1303, 1401, 1403, 1405 leaves the recognition space 630, 740, 830, 850, 1340 or newly enters the recognition space 630, 740, 830, 850, 1340 while the display module 350 is displaying the exercise content, based on the second signal.

According to an embodiment, the processor 330, 414 may be configured to, when it is identified based on the second signal that the portable device 101, 200, 430, 720, 820, 930, 1003, 1201, 1203, 1205, 1301, 1303, 1401, 1403, 1405 leaves the recognition space 630, 740, 830, 850, 1340, remove a content object corresponding to the leaving portable device 101, 200, 430, 720, 820, 930, 1003, 1201, 1203, 1205, 1301, 1303, 1401, 1403, 1405 from the exercise content, and when it is identified based on the second signal that the portable device 101, 200, 430, 720, 820, 930, 1003, 1201, 1203, 1205, 1301, 1303, 1401, 1403, 1405 newly enters the recognition space 630, 740, 830, 850, 1340, add a content object corresponding to the newly entering portable device 101, 200, 430, 720, 820, 930, 1003, 1201, 1203, 1205, 1301, 1303, 1401, 1403, 1405 to the exercise content.

According to an embodiment, the processor 330, 414 may be configured to identify whether the portable device 101, 200, 430, 720, 820, 930, 1003, 1201, 1203, 1205, 1301, 1303, 1401, 1403, 1405 is a plurality of portable devices 101, 200, 430, 720, 820, 930, 1003, 1201, 1203, 1205, 1301, 1303, 1401, 1403, 1405, based on the second signal, when it is identified that the plurality of portable devices 101, 200, 430, 720, 820, 930, 1003, 1201, 1203, 1205, 1301, 1303, 1401, 1403, 1405 move to new positions, track the new positions of the plurality of portable devices 101, 200, 430, 720, 820, 930, 1003, 1201, 1203, 1205, 1301, 1303, 1401, 1403, 1405, and reconstruct the exercise content by adjusting at least one of positions of content objects corresponding to the plurality of portable devices 101, 200, 430, 720, 820, 930, 1003, 1201, 1203, 1205, 1301, 1303, 1401, 1403, 1405, exercise information of the content objects, or size of the content objects based on the tracked positions.

According to an embodiment, the exercise content may include at least one of a content object corresponding to a user wearing the portable device 101, 200, 430, 720, 820, 930, 1003, 1201, 1203, 1205, 1301, 1303, 1401, 1403, 1405, and exercise information of the user wearing the portable device 101, 200, 430, 720, 820, 930, 1003, 1201, 1203, 1205, 1301, 1303, 1401, 1403, 1405.

According to an embodiment, an operating method of an electronic device 102, 300, 410, 510, 610, 710, 810, 910, 1001, 1220, 1320, 1420, 1510 may include operation 1610 of scanning to identify whether there is at least one portable device 101, 200, 430, 720, 820, 930, 1003, 1201, 1203, 1205, 1301, 1303, 1401, 1403, 1405 using a plurality of antennas 310, 417, 911, 913, 915, 917 for wireless communication, operation 1620 of defining a three-dimensional recognition space 630, 740, 830, 850, 1340 based on a first signal transmitted from the portable device 101, 200, 430, 720, 820, 930, 1003, 1201, 1203, 1205, 1301, 1303, 1401, 1403, 1405 for space setting, operation 1630 of calculating a position of the portable device 101, 200, 430, 720, 820, 930, 1003, 1201, 1203, 1205, 1301, 1303, 1401, 1403, 1405 in the recognition space 630, 740, 830, 850, 1340 based on a second signal transmitted from the portable device 101, 200, 430, 720, 820, 930, 1003, 1201, 1203, 1205, 1301, 1303, 1401, 1403, 1405, operation 1640 of generating exercise content based on the position of the portable device 101, 200, 430, 720, 820, 930, 1003, 1201, 1203, 1205, 1301, 1303, 1401, 1403, 1405, and operation 1650 of displaying the exercise content.

The defining of the recognition space 630, 740, 830, 850, 1340 may include providing a user of the portable device 101, 200, 430, 720, 820, 930, 1003, 1201, 1203, 1205, 1301, 1303, 1401, 1403, 1405 with a guide to guide the portable device 101, 200, 430, 720, 820, 930, 1003, 1201, 1203, 1205, 1301, 1303, 1401, 1403, 1405 to be positioned in a boundary area of the recognition space 630, 740, 830, 850, 1340 in which the exercise content is to be utilized, in response to a space setting mode being started in the portable device 101, 200, 430, 720, 820, 930, 1003, 1201, 1203, 1205, 1301, 1303, 1401, 1403, 1405 for setting the recognition space 630, 740, 830, 850, 1340, receiving the first signal transmitted from the portable device 101, 200, 430, 720, 820, 930, 1003, 1201, 1203, 1205, 1301, 1303, 1401, 1403, 1405 in the boundary area according to the guide, and defining the recognition space 630, 740, 830, 850, 1340 using the first signal received by each of the plurality of antennas 310, 417, 911, 913, 915, 917, when each of the plurality of antennas 310, 417, 911, 913, 915, 917 successfully receives the first signal.

The electronic device according to the embodiments disclosed herein may be one of various types of electronic devices. The electronic device may include, for example, a portable communication device (e.g., a smartphone), a computer device, a portable multimedia device, a portable medical device, a camera, a wearable device, a home appliance device, or the like. According to an embodiment of the disclosure, the electronic device is not limited to those electronic devices described above.

It should be appreciated that embodiments of the present disclosure and the terms used therein are not intended to limit the technological features set forth herein to particular embodiments and include various changes, equivalents, or replacements for a corresponding embodiment. In connection with the description of the drawings, like reference numerals may be used for similar or related components. It is to be understood that a singular form of a noun corresponding to an item may include one or more of the things, unless the relevant context clearly indicates otherwise. As used herein, "A or B", "at least one of A and B", "at least one of A or B", "A, B or C", "at least one of A, B and C", and "at least one of A, B, or C", each of which may include any one of the items listed together in the corresponding one of the phrases, or all possible combinations thereof. Terms such as "first", "second", or "first" or "second" may simply be used to distinguish the component from other components in question, and do not limit the components in other aspects (e.g., importance or order). It is to be understood that if an element (e.g., a first element) is referred to, with or without the term "operatively" or "communicatively", as "coupled with", "coupled to", "connected with", or "connected to" another element (e.g., a second element), the element may be coupled with the other element directly (e.g., wiredly), wirelessly, or via a third element.

As used in connection with various embodiments of the disclosure, the term "module" may include a unit implemented in hardware, software, or firmware, or any combination thereof, and may interchangeably be used with other terms, for example, "logic", "logic block", "part", or "circuitry". A module may be a single integral component, or a minimum unit or part thereof, adapted to perform one or more functions. For example, according to an embodiment, the module may be implemented in a form of an application-specific integrated circuit (ASIC).

Embodiments as set forth herein may be implemented as software (e.g., the program 140) including one or more instructions that are stored in a storage medium (e.g., an internal memory 136 or an external memory 138) that is readable by a machine (e.g., the electronic device 101 of FIG. 1). For example, a processor (e.g., the processor 120) of the machine (e.g., the electronic device 101) may invoke at least one of the one or more instructions stored in the storage medium, and execute it. This allows the machine to be operated to perform at least one function according to the at least one instruction invoked. The one or more instructions may include code generated by a compiler or code executable by an interpreter. The machine-readable storage medium may be provided in the form of a non-transitory storage medium. Here, the term "non-transitory" storage medium may, for example, refer to a tangible device, and does not include a signal (e.g., an electromagnetic wave), but this term does not differentiate between where data is semi-permanently stored in the storage medium and where the data is temporarily stored in the storage medium.

According to an embodiment, a method according to an embodiment of the disclosure may be included and provided in a computer program product. The computer program product may be traded as a product between a seller and a buyer. The computer program product may be distributed in the form of a machine-readable storage medium (e.g., a compact disc read-only memory (CD-ROM)), or be distributed (e.g., downloaded or uploaded) online via an application store (e.g., PlayStore™), or between two user devices (e.g., smartphones) directly. If distributed online, at least part of the computer program product may be temporarily generated or at least temporarily stored in the machine-readable storage medium, such as a memory of the manufacturer's server, a server of the application store, or a relay server.

According to embodiments, each component (e.g., a module or a program) of the above-described components may include a single entity or multiple entities, and some of the multiple entities may be separately disposed in different components. According to various embodiments, one or more of the above-described components or operations may be omitted, or one or more other components or operations may be added. Alternatively or additionally, a plurality of components (e.g., modules or programs) may be integrated into a single component. In such a case, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

While the disclosure has been illustrated and described with reference to various example embodiments, it will be understood that the various example embodiments are intended to be illustrative, not limiting. It will be further understood by those skilled in the art that various changes in form and detail may be made without departing from the true spirit and full scope of the disclosure, including the appended claims and their equivalents. It will also be understood that any of the embodiment(s) described herein may be used in conjunction with any other embodiment(s) described herein.

What is claimed is:

1. An electronic device, comprising:
a plurality of antennas for wireless communication;
a processor configured to scan to identify whether there is at least one portable device using the plurality of antennas, define a three-dimensional recognition space based on a first signal for space setting transmitted from a portable device identified by the scan, calculate a position of the identified portable device in the recognition space based on a second signal transmitted from the portable device, and generate exercise content based on the position of the portable device; and
a display module, including a display, configured to display the exercise content.

2. The electronic device of claim 1, wherein
the processor is configured to define the recognition space relative to a front side of the display module based on the first signal.

3. The electronic device of claim 2, wherein
the processor is configured to calculate a first relative position comprising a distance and an angle between the electronic device and the identified portable device in the recognition space using a difference in times at which the plurality of antennas receive the second signal.

4. The electronic device of claim 2, wherein
the processor is configured to identify whether the identified portable device is positioned in the recognition space based on the first relative position.

5. The electronic device of claim 4, wherein
the processor is configured to, when it is identified that the identified portable device is not positioned in the recognition space, reconstruct the exercise content by deleting a content object corresponding to the identified portable device from the exercise content.

6. The electronic device of claim 4, wherein
the processor is configured to:
when it is identified that the identified portable device is positioned in the three-dimensional recognition space,
determine whether identification information of the identified portable device is pre-enrolled information, and
reconstruct the exercise content with a content object corresponding to the identified portable device according to whether the identification information is pre-enrolled information.

7. The electronic device of claim 6, wherein
the processor is configured to, when it is determined that the identification information of the identified portable device is pre-enrolled information, update a position of the content object corresponding to the identified portable device displayed in the exercise content, based on the first relative position.

8. The electronic device of claim 6, wherein
the processor is configured to, when it is determined that the identification information of the identified portable device is not pre-enrolled information, add a content object corresponding to the position of the identified portable device to the exercise content.

9. The electronic device of claim 2, wherein
the processor is configured to, when the identified portable device includes a plurality of portable devices, calculate second relative positions between the plurality of portable devices based on first relative positions between the electronic device and the plurality of portable devices.

10. The electronic device of claim 2, wherein
the processor is configured to identify whether the identified portable device leaves the recognition space or newly enters the recognition space while the display module is displaying the exercise content, based on the second signal.

11. The electronic device of claim 10, wherein
the processor is configured to:
when it is identified based on the second signal that the identified portable device leaves the recognition space, remove a content object corresponding to the leaving portable device from the exercise content, and
when it is identified based on the second signal that the identified portable device newly enters the recognition space, add a content object corresponding to the newly entering portable device to the exercise content.

12. The electronic device of claim 2, wherein
the processor is configured to:
identify whether the identified portable device includes a plurality of portable devices, based on the second signal,
when it is identified that the plurality of portable devices move to new positions, track the new positions of the plurality of portable devices, and
reconstruct the exercise content by adjusting at least one of positions of content objects corresponding to the plurality of portable devices, exercise information of the content objects, or size of the content objects based on the tracked positions.

13. The electronic device of claim 1, wherein
the processor is configured to:
provide a user of the identified portable device with a guide to guide the identified portable device to be positioned in a boundary area of the recognition space in which the exercise content is to be utilized, in response to a space setting mode for setting the recognition space being started in the identified portable device, and set the plurality of antennas to receive the first signal transmitted from the identified portable device according to the guide.

14. The electronic device of claim 13, wherein
the processor is configured to provide a guide to guide the identified portable device to move to another boundary area next to the boundary area, when each of the plurality of antennas successfully receives the first signal transmitted from the identified portable device in the boundary area according to the guide.

15. The electronic device of claim 14, wherein
the processor is configured to define the recognition space using the first signal received by each of the plurality of antennas, when each of the plurality of antennas successfully receives the first signal.

16. The electronic device of claim 1, wherein
one or more of the plurality of antennas are disposed at each of two or more symmetrical positions among top, bottom, left, and right of the display module, and
the processor is configured to calculate a first relative position between the electronic device and the identified portable device using a difference in times at which the plurality of antennas disposed at the symmetrical positions receive the second signal.

17. The electronic device of claim 1, wherein
the exercise content comprises at least one of:
a content object corresponding to a user wearing the identified portable device; and
exercise information of the user wearing the identified portable device.

18. An operating method of an electronic device, the operating method comprising:
scanning to identify whether there is at least one portable device using a plurality of antennas for wireless communication;
defining a three-dimensional recognition space based on a first signal for space setting transmitted from a portable device identified by the scan;
calculating a position of the identified portable device in the recognition space based on a second signal transmitted from the identified portable device;
generating exercise content based on the position of the identified portable device; and
displaying the exercise content.

19. The operating method of claim 18, wherein
the defining of the recognition space comprises:
providing a user of the identified portable device with a guide to guide the identified portable device to be positioned in a boundary area of the recognition space in which the exercise content is to be utilized, in response to a space setting mode for setting the recognition space being started in the portable device;
receiving the first signal transmitted from the identified portable device in the boundary area according to the guide; and
defining the recognition space using the first signal received by each of the plurality of antennas, when each of the plurality of antennas successfully receives the first signal.

20. The operating method of claim 18, wherein
the generating of the exercise content comprises:
calculating a first relative position comprising a distance and an angle between the electronic device and the identified portable device using a difference in times at which the plurality of antennas receive the second signal;
identifying whether the identified portable device is positioned in the recognition space based on the first relative position;
reconstructing the exercise content by deleting a content object corresponding to the identified portable device from the exercise content, when it is identified that the identified portable device is not positioned in the recognition space; and
reconstructing the exercise content with a content object corresponding to the identified portable device according to whether identification information of the identified portable device is pre-enrolled information, when it is identified that the identified portable device is positioned in the three-dimensional recognition space.

* * * * *